(12) United States Patent
Deem et al.

(10) Patent No.: US 8,636,684 B2
(45) Date of Patent: *Jan. 28, 2014

(54) METHODS AND SYSTEMS FOR TOXIN DELIVERY TO THE NASAL CAVITY

(75) Inventors: Mark E. Deem, Mountain View, CA (US); Hanson Gifford, Woodside, CA (US)

(73) Assignee: The Foundry LLC, Menlo Park, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 13/328,203

(22) Filed: Dec. 16, 2011

(65) Prior Publication Data

US 2012/0089078 A1   Apr. 12, 2012

Related U.S. Application Data

(60) Continuation of application No. 12/636,477, filed on Dec. 11, 2009, now Pat. No. 8,105,817, which is a division of application No. 11/750,963, filed on May 18, 2007, now Pat. No. 7,655,243, which is a continuation-in-part of application No. 11/459,090, filed on Jul. 21, 2006, now Pat. No. 7,608,275.

(60) Provisional application No. 60/702,077, filed on Jul. 22, 2005, provisional application No. 60/747,771, filed on May 19, 2006.

(51) Int. Cl.
*A61K 9/22* (2006.01)
*A61N 1/30* (2006.01)

(52) U.S. Cl.
USPC .................. 604/19; 604/890.1; 604/891.1

(58) Field of Classification Search
None
See application file for complete search history.

(56) References Cited

U.S. PATENT DOCUMENTS

| | | |
|---|---|---|
| 1,695,107 A | 12/1928 | Kahl |
| 2,566,806 A | 9/1951 | Miller |
| 3,469,139 A | 9/1969 | Colvin |
| 3,788,296 A | 1/1974 | Klatt et al. |
| 3,918,449 A | 11/1975 | Pistor |
| 4,767,402 A | 8/1988 | Kost et al. |
| 5,056,529 A | 10/1991 | de Groot |
| 5,139,029 A | 8/1992 | Fishman et al. |
| 5,286,254 A | 2/1994 | Shapland et al. |
| 5,766,605 A | 6/1998 | Sanders et al. |
| 5,496,304 A | 10/1998 | Krespi |
| 5,817,073 A | 10/1998 | Krespi |
| 5,820,589 A | 10/1998 | Torgerson et al. |
| 5,964,223 A | 10/1999 | Baran |
| 6,063,768 A | 5/2000 | First |
| 6,139,845 A | 10/2000 | Donovan |
| 6,265,379 B1 | 7/2001 | Donovan |
| 6,306,423 B1 | 10/2001 | Donovan et al. |
| 6,358,926 B2 | 3/2002 | Donovan |
| 6,361,554 B1 | 3/2002 | Brisken |
| 6,383,509 B1 | 5/2002 | Donovan et al. |
| 6,425,887 B1 | 7/2002 | McGuckin et al. |
| 6,432,092 B2 | 8/2002 | Miller |
| 6,447,785 B1 | 9/2002 | Donovan |
| 6,448,231 B2 | 9/2002 | Graham |
| 6,464,680 B1 | 10/2002 | Brisken et al. |
| 6,475,160 B1 | 11/2002 | Sher |
| 6,488,673 B1 | 12/2002 | Laufer et al. |
| 6,506,399 B2 | 1/2003 | Donovan |
| 6,526,976 B1 | 3/2003 | Baran |
| 6,546,932 B1 | 4/2003 | Nahon et al. |
| 6,601,581 B1 | 8/2003 | Babaev |
| 6,620,415 B2 | 9/2003 | Donovan |
| 6,623,742 B2 | 9/2003 | Voet |
| 6,626,855 B1 | 9/2003 | Weng et al. |
| 6,632,440 B1 | 10/2003 | Quinn et al. |
| 6,645,496 B2 | 11/2003 | Aoki et al. |
| 6,649,161 B1 | 11/2003 | Donovan |
| 6,719,694 B2 | 4/2004 | Weng et al. |
| 6,740,321 B1 | 5/2004 | Donovan |
| 6,767,544 B2 | 7/2004 | Brooks et al. |
| 6,773,711 B2 | 8/2004 | Voet |
| 6,776,991 B2 | 8/2004 | Naumann |
| 6,827,931 B1 | 12/2004 | Donovan |
| 6,838,434 B2 | 1/2005 | Voet |
| 6,841,156 B2 | 1/2005 | Aoki et al. |
| 6,843,998 B1 | 1/2005 | Steward et al. |
| 6,847,849 B2 | 1/2005 | Mamo et al. |
| 6,861,058 B2 | 3/2005 | Aoki et al. |

(Continued)

FOREIGN PATENT DOCUMENTS

WO   WO 2004/048519 A2   6/2004
WO   WO 2004/048519 A3   7/2004

(Continued)

OTHER PUBLICATIONS

Rohrbach et al (Ann Otol Rhinol Laryngol vol. 110, pp. 1045-1050, 2001).*

(Continued)

*Primary Examiner* — Albert Navarro
(74) *Attorney, Agent, or Firm* — Wilson, Sonsini, Goodrich & Rosati

(57) ABSTRACT

Methods and systems for delivering toxin and toxin fragments to a patient's nasal cavity provide for both release of the toxin and delivery of energy which selectively porates target cells to enhance uptake of the toxin. The use of energy-mediated delivery is particularly advantageous with light chain fragment toxins which lack cell binding capacity.

72 Claims, 24 Drawing Sheets

(56) References Cited

U.S. PATENT DOCUMENTS

| | | | |
|---|---|---|---|
| 6,872,397 | B2 | 3/2005 | Aoki et al. |
| 6,974,578 | B1 | 12/2005 | Aoki et al. |
| 7,238,357 | B2 | 7/2007 | Barron |
| 7,608,275 | B2 | 10/2009 | Deem et al. |
| 7,655,243 | B2 | 2/2010 | Deem et al. |
| 8,105,817 | B2 * | 1/2012 | Deem et al. ............ 435/283.1 |
| 2001/0044596 | A1 | 11/2001 | Jaafar |
| 2002/0082197 | A1 | 6/2002 | Aoki et al. |
| 2002/0111620 | A1 | 8/2002 | Cooper et al. |
| 2002/0198512 | A1 | 12/2002 | Seward |
| 2003/0018344 | A1 | 1/2003 | Kaji et al. |
| 2003/0050591 | A1 | 3/2003 | McHale |
| 2003/0113349 | A1 * | 6/2003 | Coleman, III ............ 424/239.1 |
| 2003/0153881 | A1 | 8/2003 | Roche et al. |
| 2003/0202990 | A1 | 10/2003 | Donovan et al. |
| 2003/0211121 | A1 | 11/2003 | Donovan |
| 2004/0009180 | A1 | 1/2004 | Donovan |
| 2004/0010290 | A1 | 1/2004 | Schroeppel et al. |
| 2004/0086531 | A1 | 5/2004 | Barron |
| 2004/0091880 | A1 | 5/2004 | Wiebusch et al. |
| 2004/0142005 | A1 | 7/2004 | Brooks et al. |
| 2004/0151741 | A1 | 8/2004 | Borodic |
| 2004/0175399 | A1 | 9/2004 | Schiffman |
| 2004/0186435 | A1 | 9/2004 | Seward |
| 2004/0213813 | A1 | 10/2004 | Ackerman |
| 2004/0213814 | A1 | 10/2004 | Ackerman |
| 2004/0226556 | A1 | 11/2004 | Deem et al. |
| 2004/0253274 | A1 | 12/2004 | Voet |
| 2005/0019346 | A1 | 1/2005 | Boulis |
| 2005/0074461 | A1 | 4/2005 | Donovan |
| 2005/0107853 | A1 | 5/2005 | Krespi et al. |
| 2005/0152924 | A1 | 7/2005 | Voet |
| 2005/0281751 | A1 | 12/2005 | Levin |
| 2006/0008462 | A1 | 1/2006 | Sanders |
| 2006/0106361 | A1 | 5/2006 | Muni et al. |
| 2006/0222667 | A1 | 10/2006 | Deem et al. |
| 2006/0225742 | A1 | 10/2006 | Deem et al. |
| 2007/0021803 | A1 | 1/2007 | Deem et al. |
| 2007/0267011 | A1 | 11/2007 | Deem et al. |
| 2010/0003282 | A1 | 1/2010 | Deem et al. |
| 2010/0087775 | A1 | 4/2010 | Deem et al. |

FOREIGN PATENT DOCUMENTS

| | | | |
|---|---|---|---|
| WO | WO 2004/101028 A2 | 11/2004 | |
| WO | WO 2004/101028 A3 | 12/2006 | |
| WO | WO 2007/014003 A2 | 2/2007 | |
| WO | WO 2007/014003 A3 | 10/2007 | |

OTHER PUBLICATIONS

Ahnert-Hilger, et al. Introduction of macromolecules into bovine adrenal medullary chromaffin cells and rat pheochromocytoma cells (PC12) by permeabilization with streptolysin O: inhibitory effect of tetanus toxin on catecholamine secretion. J Neurochem. Jun. 1989;52(6):1751-8.

Bigalke, et al. Clostridal toxins. Handbook of Experimental Pharmacology. 2000; 145:407-443.

Bittner, et al. Isolated light chains of botulinum neurotoxins inhibit exocytosis. Studies in digitonin-permeabilized chromaffin cells. J Biol Chem. Jun. 25, 1989;264(18):10354-60.

Blindt, et al. Development of a new biodegradable intravascular polymer stent with stimultaneous incorporation of bioactive substances. Int J Artif Organs. Dec. 1999;22(12):843-53.

Buzzi. Diphtheria toxin treatment of human advanced cancer. Cancer Res. May 1982;42(5):2054-8.

Chaddock, et al. Expression and purification of catalytically active, non-toxic endopeptidase derivatives of Clostridium botulinum toxin A. Protein Expr Purif. Jul. 2002;25(2):219-28.

Chang. Cell poration and cell fusion using an oscillating electric filed. Biophys J. Oct. 1989;56(4):641-52.

De Paiva, et al. Light chain of botulinum neurotoxin is active in mammalian motor nerve terminals when delivered via liposomes. FEBS Lett. Dec. 17, 1990;277(1-2):171-4.

Guzman, et al. Bioeffects caused by changes in acoustic cavitation bubble density and cell concentration: a unified explanation based on cell-to-bubble ratio and blast radius. Ultrasound Med Biol. Aug. 2003;29(8):1211-22.

Kistner, et al. Reductive cleavage of tetanus toxin and botulinum neurotoxin A by the thioredoxin system from brain. Evidence for two redox isomers of tetanus toxin. Naunyn Schmiedebergs Arch Pharmacol. Feb. 1992;345(2):227-34.

Korpela, et al. Comparison of tissue reactions in the tracheal mucosa surrounding a bioabsorbable and silicone airways stents. Ann Thorac Surg. Nov. 1998;66(5):1772-6.

Kreitman. Taming ricin toxin. Nat Biotechnol. Apr. 2003;21(4):372-4.

Raj. Editorial, Pain Practice. 2004; 4(1S):S1-S3.

Shaari, et al. Rhinorrhea is decreased in dogs after nasal application of botulinum toxin. Otolaryngol Head Neck Surg. Apr. 1995;112(4):566-71.

Simpson, et al. Isolation and Characterization of the Botulinum neurotoxins. Methods Enzymol. 1998;165:76-85.

Sundaram, et al. An experimental and theoretical analysis of ultrasound-induced permeabilization of cell membranes. Biophys J. May 2003;84(5):3087-101.

Tsuji, et al. Biodegradable stents as a platform to drug loading. Int J Cardiovasc Intervent. 2003;5(1):13-6.

Unal, et al. Effect of botulinum toxin type A on nasal symptoms in patients with allergic rhinitis: a double-blind, placebo-controlled clinical trial. Acta Otolaryngol. Dec. 2003;123(9):1060-3.

Weaver, et al. Electroporation: a general phenomenon for manipulating cells and tissues. J Cell Biochem. Apr. 1993;51(4):426-35.

International search report and written opinion dated Mar. 3, 2008 for PCT/US2007/069391.

European search report and opinion dated Jun. 18, 2010 for EP Application No. 07784000.7.

* cited by examiner

FIG. 1

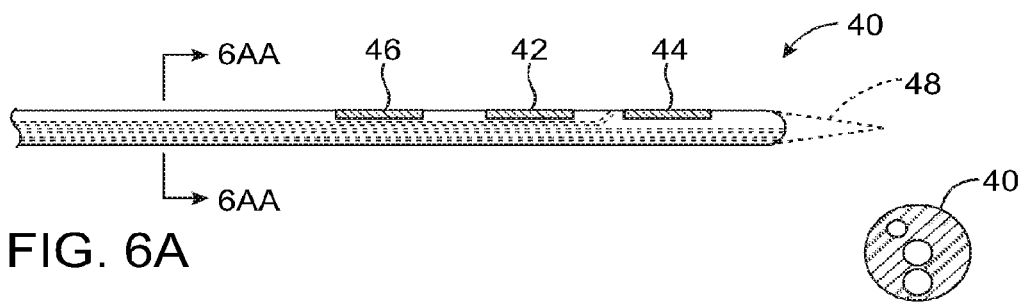
FIG. 6A
FIG. 6AA
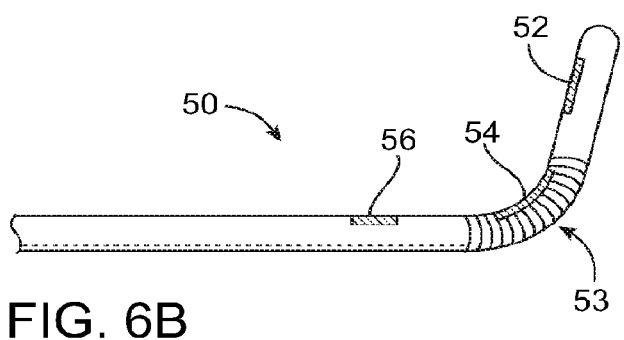
FIG. 6B
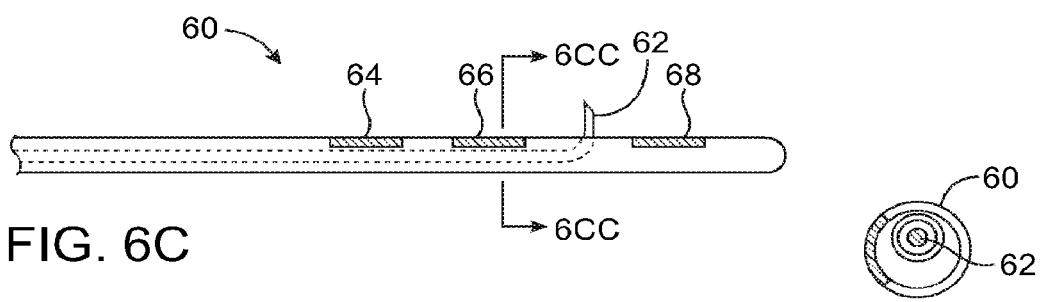
FIG. 6C
FIG. 6CC
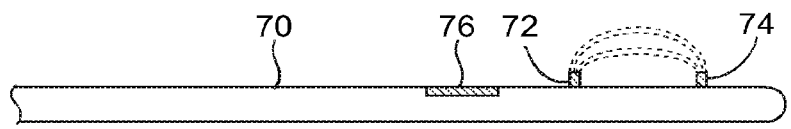
FIG. 6D

METHODS AND SYSTEMS FOR TOXIN DELIVERY TO THE NASAL CAVITY

CROSS-REFERENCES TO RELATED APPLICATIONS

The present application is a continuation of application Ser. No. 12/636,477, filed on Dec. 11, 2009, which is a divisional of application Ser. No. 11/750,963, filed on May 18, 2007, which is a continuation-in-part of application Ser. No. 11/459,090, filed on Jul. 21, 2006, which claimed the benefit of provisional application No. 60/702,077, filed on Jul. 22, 2005, and of provisional application No. 60/747,771, filed on May 19, 2006, the full disclosures of which are incorporated herein by reference.

BACKGROUND OF THE INVENTION

1. Field of the Invention

The present invention relates generally to medical methods and systems. More particularly, the present invention relates to methods and systems for delivering toxins, such as botulinum toxin light chain fragments, to target cells in a nasal cavity.

Rhinitis, which includes the symptoms of rhinorrhea, is a condition resulting from inflammation and swelling of the patient's mucus membranes which line the nasal cavity Rhinitis and/or rhinorrea can arise from a number of conditions, most often results from allergies to pollen, dust, seasonal allergens or other airborne substances, but can also be caused by anatomic pathologies such as blockages (as in the case of sinusitis). Symptoms may include sneezing, itching, nasal congestion, and a runny nose.

While numerous treatments for rhinitis have been proposed over the years, no single treatment is optimum for all patients or all conditions. Most commonly, hay fever and other forms of rhinitis are treated with antihistamines which block the inflammatory response. While effective, many antihistamines can cause drowsiness, have a limited duration of effect, and present the patient with an on-going cost to continuously purchase the drugs.

Recently, a longer term therapy for rhinitis which relies on the use of botulinum toxin ("BoNT") for blocking mucus production by mucus-producing cells in the nasal membrane has been proposed. Botulinum and other neurotoxins are capable of disabling adrenergic cells, including epithelial or goblet cells which are responsible for the majority of mucus production in the nasal cavity membrane. Dr. Ira Sanders has demonstrated that introduction of intact botulinum toxin molecules into the nasal passages of canines can reduce mucus secretion by a significant amount.

While the experimental work of Dr. Sanders holds promise for long term rhinitis treatment, it faces a number of challenges before it is suitable for wide spread use in humans. In particular, botulinum toxin is a neurotoxin which could have significant negative effects on a patient if accidentally released outside of the targeted nasal passages. Inadvertent distribution of the toxin to muscles of the oropharynx, mouth, tongue, or elsewhere could result in serious complications to the patient. Additionally, the use of botulinum-soaked gauze pads for delivering the toxin to the nasal cavities, as demonstrated by Dr. Sanders, will have limited ability to uniformly and selectively deliver the botulinum to the regions having high concentrations of preferred target cells, such as epithelial or goblet cells in the nasopharynx.

For these reasons, it would be desirable to provide improved methods and systems for delivering toxins, such as botulinum and active botulinum fragments, to the nasal membrane of a patient, particularly a patient suffering from rhinitis or other conditions associated with nasal inflammation and conditions, such as sinus headaches and migraine headaches. The methods and systems should be capable of providing for selective and repeatable delivery of the toxins to defined target areas within the nasal cavities, including particular paranasal sinuses, the nasopharynx, and in some cases substantially the entire nasal cavity. The systems and methods should provide for the safe and effective delivery of the toxins, and in particular should reduce or eliminate the risk of toxin being delivered to non-targeted tissues outside of the nasal cavity. At least some of these objectives will be met by the inventions described herein below.

2. Description of the Background Art

U.S. Pat. No. 5,766,605, to Sanders et al. has been described above. Sharri et al. (1995) *Otolaryngol. Head Neck Surg.* 112: 566-571 also reports the work of Dr. Sanders described in the '605 patent. Ünal et al. (2002) *Acta Otolaryngol* 123: 1060-1063 describes the injection of botulinum toxin A into the turbinates of patients suffering from allergic rhinitis. See also, U.S. Pat. No. 6,974,578. The purification and possible therapeutic uses of botulinum light chain are described in US2004/0151741, US2005/0019346, and Chaddock et al. (2002) *Protein Expression and Purification* 25: 219-228. Energy-mediated transdermal delivery of intact botulinum toxin is suggested in US2005/007441 and 2004/0009180. The use of catheters and other devices for the energy-mediated delivery of botulinum light chain is described in commonly owned co-pending provisional application 60/702,077, filed Jul. 22, 2005, the full disclosure of which has previously been incorporated herein by reference.

BRIEF SUMMARY OF THE INVENTION

The present invention provides treatments for any disease or condition for which rhinorrhea is a result or symptom.

Rhinorrhea is the term describing the effluence of mucus from the lining of the nasal passages, nasopharynx, or paranasal sinuses Rhinorrhea can be a symptom of a number of diseases such as the common cold, sinusitis or rhinitis, Rhinitis (inflammation of the airways) falls into two major categories—allergic and non-allergic (or vasomotor) rhinitis. Each can have several subcategories. Sinusitis is an infection or inflammation of the paranasal sinuses. Sinusitis may have a number of different causes, and can be the result of chronic inflammation of the nasal passages, for example as a result of chronic rhinitis.

Allergic rhinitis is an immunologic response modulated by IgE and characterized predominantly by sneezing, rhinorrhea, nasal congestion, and pruritus of the nose. It may be seasonal (a condition commonly referred to as hay fever) or perennial. The seasonal form is caused by allergens released during tree, grass, or weed pollination, whereas the perennial form is caused by allergies to animal dander, dust mites, or mold spores with or without associated pollinosis. Data also suggest that urban air pollutants from automobiles and other sources may have an adjunctive effect.

Nonallergic rhinitis is a diagnosis of rhinitis without any immunoglobulin E (IgE) mediation, as documented by allergen skin testing. Hence, the rhinorrhea, sneezing, pruritus, and congestion do not result from allergy or hypersensitivity and continue to persist, whether continuously or sporadically. Nonallergic rhinitis affects 5-10% of the population. Nonallergic rhinitis has 7 basic subclassifications, including infectious rhinitis, nonallergic rhinitis with eosinophilia syndrome (NARES), occupational rhinitis, hormonal rhinitis, drug-induced rhinitis, gustatory rhinitis, and vasomotor rhinitis Patients may or may not present with the same symptoms seen in allergic rhinitis.

According to the present invention, botulinum toxin, ricin, exotoxin A, diphtheria toxin, cholera toxin, tetanus toxin, other neurotoxins, and active fragments thereof are delivered to a patient's nasal membrane while applying energy to target cells within the membrane under conditions which cause a reversible (or in some instances non-reversible) poration of the cell membranes to enhance delivery of the toxin into the cells. The region where the toxin is introduced may comprise any portion of the nasal cavity, such as a single paranasal sinus or portion thereof, a main nasal passage, two or more paranasal sinuses, or in some cases may comprise substantially the entire nasal cavity of the patient. A particular target region for the toxin may comprise the nasopharynx which is at the back of the nasal passage. The nasopharynx comprises a cluster of epithelial or goblet cells which are responsible for mucus secretion and which are susceptible to the disabling mechanism of the botulinum toxin and other neurotoxins.

The energy is preferably selectively applied to a targeted region containing a variety of cell types, including goblet cells, epithelial cells, ciliated and non-ciliated columnar cells, basal cells, and less or no energy applied to untargeted regions. It will be appreciated that the energy may be applied to regions of the nasal membrane which are the same or different from the regions to which the toxin has been introduced. By controlling the delivery area of both the toxin delivery and the energy delivery, the methods and apparatus of the present invention can more specifically target the epithelial or goblet and other recipient cells of interest while minimizing the amount of toxin which enters non-targeted cells. That is, only those cells in the nasal membrane which are exposed to both the toxin and the applied energy will preferentially be permeablized or porated to receive the toxin within the cytoplasm of the cell.

The toxin to be delivered may comprise any neurotoxin capable of disabling mucus secretion in epithelial or goblet cells and other mucus-producing nasal cells. Preferably, the toxin comprises botulinum toxin, although other toxins such as ricin, exotoxin A, diphtheria toxin, cholera toxin, tetanus toxin, other neurotoxins, and active fragments thereof may also find use. In preferred aspects of the present invention, only an active fragment of the toxin will be delivered to the nasal cavity. Botulinum toxin and the other toxins listed above commonly comprise both a heavy chain and a light chain. The heavy chain is responsible for binding to the target cells and mediating passage of the light chain into the cytoplasm of the target cells. By delivering only the light or active chain of these toxins (after removal of the heavy chain or recombinant production of only the light chain), the risk of accidental delivery of the toxin to non-target cells is greatly reduced. Delivery of the active or light chain fragments into the target cells, according to the present invention, is mediated and enhanced by the selective application of an energy which porates the cell membrane to allow entry of the light chain or active fragment. The presently preferred botulinum light chain fragment may be derived from any one of the seven presently known botulinum types A-G.

Any type of energy which is capable of reversibly permeablizing or porating the cell wall to allow passage of the toxin molecule, either whole toxin or preferably light chain fragment, into the cell cytoplasm may be applied to the cell membrane. Thus, energy may comprise various forms of electrical pulses, acoustic pulses, X-ray energy, microwave energy, or the like, and combinations thereof. Preferably, the energy will be either pulsed electrical energy of the type which is commonly used for cellular electroporation or will be ultrasonic energy of the type commonly employed for sonoporation of cells. The energy may be applied using the same catheters or other structures which are used for delivering the toxins. Alternatively, the energy may be applied using separate external or internal sources, such as using separate external ultrasonic transducers and/or ultrasound wave guides capable of delivering focused or unfocused ultrasound into the target tissues of the nasal cavity.

In specific embodiments of the methods of the present invention, the toxin may be introduced to the target region through a catheter. For example, the catheter may carry a balloon which engages the nasal membrane in order to effect delivery of the toxin to the target cells. In a particular example, the balloon is porous over at least a portion of its area so that the toxin may be released to specific areas of the nasal membrane, typically being incorporated into a suitable liquid, gel, or other fluid or fluidizable carrier. In other embodiments, the toxin may be introduced through one or more needles carried on the catheter, and in still other embodiments the toxin may be aerosolized from a small port, nozzle, or other orifice or structure on the catheter.

While the energy may be applied from a separate external source, as generally described above, the energy will most often be applied from the same catheter or other apparatus used to deliver the toxin. For example, when ultrasonic or other acoustic energy is being applied, the transducer may be on or associated with the catheter. In a particular example, it is shown that the transducer may be located within or beneath the porous balloon which is used to deliver toxin to the nasal membrane. When electrical energy is used for poration, the electrodes may be on the catheter within or surrounding the region which delivers the energy to the nasal membrane. In other instances, the energy may be applied from a separate catheter or other device adapted for intranasal introduction. In still other instances, the energy application will apply energy transcutaneously, for example from the skin of the face, typically surrounding the nose over the sinus cavities.

In addition to the methods described above, the present invention further provides systems for delivering toxins to epithelial or goblet and other target cells as defined above in a nasal membrane. The systems may typically comprise a catheter adapted to introduce a toxin to a region adjacent to the target cells. An energy applicator is further provided for applying energy to the target cells under conditions which cause a reversible poration of the cell membranes to enhance delivery of the toxin. Systems may still further comprise a source of the toxin suitable for introduction from or through the catheter. The energy applicator may be mounted on or incorporated within the catheter, or may be a separate or external source. In an exemplary embodiment, as illustrated in FIG. 18, an external applicator may comprise a mask or other structure which fits over the nose and/or sinus region of the patient and which is capable of delivering acoustic or microwave energy to the target cells within the target regions.

When the energy applicator is incorporated with or within the catheter, the delivery pattern of the energy will usually be at least partially overlapping with the toxin delivery pattern of the catheter. For example, when a porous balloon is used for toxin delivery, the acoustic transducer, electroporation electrodes, or the like, will usually be disposed to deliver energy which at least partly overlaps with the dispersion pattern of the toxin. In some instances, the region of applied energy will be coextensive with the region of toxin dispersion. In other instances, the two regions will only partially overlap. In the latter case, the delivery of the toxin will be enabled or enhanced principally within the regions of overlap.

BRIEF DESCRIPTION OF THE DRAWINGS

FIG. 1—depicts a schematic of the creation of neurotoxin Botulinum Toxin Type A (BoNT/A), including the light chain (LC) fragment or portion.

FIGS. 6A-6D, 6AA and 6CC—depict various electrode catheter configurations adapted to deliver energy or energy and therapeutic agents to target tissue.

DETAILED DESCRIPTION OF THE INVENTION

Figure 2A:
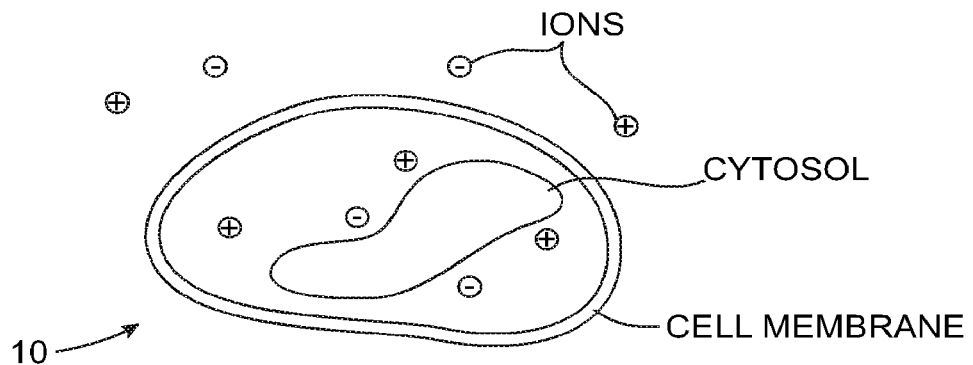
FIG. 2A—depicts a schematic of a target cell, including the cell membrane, and inner cellular matrices.

The present invention is directed to methods and systems for delivering toxins to target cells within a patient's nasal cavity. The toxins may be intact toxins, such as botulinum toxin, ricin, exotoxin A, diphtheria toxin, cholera toxin, tetanus toxin, other neurotoxins, and active fragments thereof. Each of these toxins comprises a heavy chain responsible for cell binding and a light chain having enzyme activity responsible for cell toxicity.

Botulinum toxin blocks acetylcholine release from cells, such as the epithelial or goblet cells in the nasal membranes responsible for mucus hypersecretion, and can thus be effective even without energy-mediated delivery in accordance with the principles of the present invention. The use of energy to permeablize or porate the cell membranes of the epithelial or goblet cells or other mucus-secreting cells of the nasal lining, in accordance with the present invention, allows botulinum and other toxins to be preferentially delivered to the targeted epithelial or goblet and other mucus-producing cells. Additionally, it allows use of the active or light chains of these toxins (having the heavy chains removed or inactivated) for treatments in accordance with the present invention. Normally, the light chains when separated from the cell-binding heavy chains of botulinum and the other toxins are incapable of entering the cells and thus will be free from significant cell toxicity. By using the energy-mediated protocols of the present invention, the toxin light chains may be locally and specifically introduced into the target cells located within defined regions of the nasal membrane. Thus, even if the toxin fragments are accidentally dispersed beyond the desired target regions, the fragments will not generally enter cells without the additional application of cell permeablizing or porating energy. For that reason, the toxin delivery methods of the present invention are particularly safe when performed with toxin fragments, such as the light chain of botulinum and other toxins.

While the remaining portion of this disclosure will be presented with specific reference to the botulinum toxin light chain, it will be appreciated that the energy-mediated delivery protocols and systems may also be used with other intact toxins and in particular with other light chain toxin fragments as just discussed.

Figure 1:
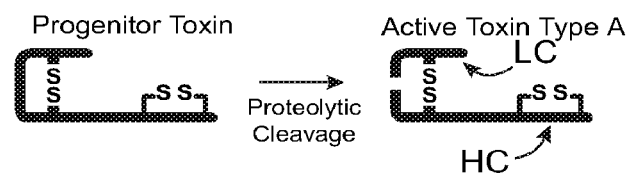

Generally, the botulinum toxin molecule (BoNT) is synthesized as a single polypeptide chain of 150 kD molecular weight. The neurotoxin is then exposed to enzymes, either during cultivation of the *Clostridium botulinum* organism or subsequent to purification of the toxin, wherein specific peptide bonds are cleaved or "nicked" resulting in the formation of a dichain molecule referred to as BoNT. As shown in FIG. 1, dichain neurotoxin is composed of a light chain region 50 kD molecular weight linked by disulfide bonds to a heavy chain 100 kD molecular weight (Kistner, A., Habermann, E. (1992) *Naunyn Schmiedebergs Arch. Pharmacol.* 345, 227-334). When the light chain is separated from the heavy chains of botulinum toxin, neither chain is capable of blocking neurotransmitter release, however, the light chain alone is capable of blocking acetylcholine release if transported directly into the cell cytosol. (Ahnert-Hilger, G., Bader, M. F., Bhakdi, S., Gratzl, M. (1989) *J. Neurochem.* 52, 1751-1758 and Simpson, L. L. (1981) *Pharmacol. Rev.* 33, 155-188.) Focusing on the light chain, the isolation or separation process essentially renders the light chain "non-toxic" in a general environment, while still maintaining its effect or toxicity, once it is transported through the target cell membrane.

Over the past several years, the separation and purification of the light chain and heavy chain of BoNT has seen significant development activity. In the case of the heavy chain (HC), researchers are interested in its ability to bond with a target cell and deliver certain molecules into that cell. For example, various drug delivery applications have been suggested, for example, using the HC to bind to tPA so that a patient could inhale the HC-bound tPA allowing it to cross the membrane of the lungs and be transported into the bloodstream for anticoagulation. Of particular interest to the present invention are the efforts to isolate and purify the light chain (LC) of the botulinum molecule. In its isolated and purified form, all HC elements are removed, rendering the LC incapable of crossing the cell membrane without assistance. This renders the LC a non-toxic protein to the cell environment, while still maintaining its encoded toxicity by, once it is effectively delivered to its appropriate catalytic environment; the cell cytosol.

Various groups have been active in the area of isolation and purification. For example, companies such as Metabiologics, a group affiliated with the University of Wisconsin, the Center for Applied Microbiology and Research (CAMR), a division of the UK Health Protection Agency, List Biological Laboratories, Inc. of California, and other research groups throughout the world. Many of these companies provide purified preparations of botulinum neurotoxins from *Clostridium botulinum* types A and B. List Laboratories in particular provides recombinantly produced light chains from both types A, B, C, D and E.

For purposes of this specification, the terms "poration" and/or "permeablization" include various forms of electrically-medicated poration, such as the use of pulsed electric fields (PEFs), nanosecond pulsed electric fields (nsPEFs), ionophoreseis, electrophoresis, electropermeabilization, as well as other energy mediated permeabilization, including sonoporation (mediated by ultrasonic or other acoustic energy), and/or combinations thereof, to create temporary pores in a targeted cell membrane. Similarly, the term "electrode" or "energy source" used herein, encompasses the use of various types of energy producing devices, including x-ray, radiofrequency (RF), DC current, AC current, microwave, ultrasound, adapted and applied in ranges to produce membrane permeabilization in the targeted cell.

Reversible electroporation, first observed in the early 1970's, has been used extensively in medicine and biology to transfer chemicals, drugs, genes and other molecules into targeted cells for a variety of purposes such as electrochemotherapy, gene transfer, transdermal drug delivery, vaccines, and the like.

In general, electroporation may be achieved utilizing a device adapted to activate an electrode set or series of electrodes to produce an electric field. Such a field can be generated in a bipolar or monopolar electrode configuration. When applied to cells, depending on the duration and strength of the applied pulses, this field operates to increase the permeabilization of the cell membrane and reversibly open the cell membrane for a short period of time by causing pores to form in the cell lipid bilayer allowing entry of various therapeutic elements or molecules, after which, when energy application ceases, the pores spontaneously close without killing the cell after a certain time delay. As characterized by Weaver, *Electroporation: A General Phenomenon for Manipulating Cells and Tissues Journal of Cellular Biochemistry*, 51:426-435 (1993), short (1-100 μs) and longer (1-10 ms) pulses have induced electroporation in a variety of cell types. In a single cell model, most cells will exhibit electroporation in the range of 1-1.5V applied across the cell (membrane potential).

In addition, it is known in the art that macromolecules can be made to cross reversibly created pores at voltages of 120V or less applied to cells for durations of 20 microseconds to many milliseconds. For applications of electroporation to cell volumes, ranges of 10 V/cm to 10,000 V/cm and pulse durations ranging from 1 nanosecond to 0.1 seconds can be applied. In one example, a relatively narrow (μsec) high voltage (200V) pulse can be followed by a longer (>mscc) lower voltage pulse (<100V). The first pulse or pulses open the pores and the second pulse or series of pulses assist in the movement of the BoNT-LC across the cell membrane and into the cell.

Certain factors affect how a delivered electric field will affect a targeted cell, including cell size, cell shape, cell orientation with respect to the applied electric field, cell temperature, distance between cells (cell-cell separation), cell type, tissue heterogeneity, properties of the cellular membrane and the like.

Various waveforms or shapes of pulses may be applied to achieve electroporation, including sinusoidal AC pulses, DC pulses, square wave pulses, exponentially decaying waveforms or other pulse shapes such as combined AC/DC pulses, or DC shifted RF signals such as those described by Chang in *Cell Poration and Cell Fusion using an Oscillating Electric Field*, Biophysical Journal October 1989, Volume 56 pgs 641-652, depending on the pulse generator used or the effect desired. The parameters of applied energy may be varied, including all or some of the following: waveform shape, amplitude, pulse duration, interval between pulses, number of pulses, combination of waveforms and the like.

There are at least two general power categories of medical ultrasound waves. One category of medical ultrasound wave is high acoustic pressure ultrasound. Another category of medical ultrasound wave is low acoustic pressure ultrasound.

Acoustic power is expressed in a variety of ways by those skilled in the art. One method of estimating the acoustic power of an acoustic wave on tissue is the Mechanical Index. The Mechanical Index (MI) is a standard measure of the acoustic output in an ultrasound system.

High acoustic pressure ultrasound systems generally have a MI greater than 10. Low acoustic pressure systems generally have a MI lower than 5. For example, diagnostic ultrasound systems are limited by law to a Mechanical Index not to exceed 1.9.

Another measurement used by those skilled in the art is the spatial peak, peak average intensity (Isppa). The intensity of an ultrasound beam is greater at the center of its cross section than at the periphery. Similarly, the intensity varies over a given pulse of ultrasound energy. Isppa is measured at the location where intensity is maximum averaged over the pulse duration. Isppa for high acoustic pressure or high intensity focused ultrasound (HIFU) applications ranges from approximately 1500 W/cm2. to 9000 W/cm2. Diagnostic ultrasound equipment, for instance, will generally have, and an Isppa less than 700 W/cm2.

Yet another way in which ultrasound waves can be characterized is by the amplitude of their peak negative pressure. High acoustic pressure or HIFU applications employ waves with peak amplitudes in excess of 10 MPa. Low acoustic pressure ultrasound will generally have peak negative pressures in the range of 0.01 to 5.0 MPa. Diagnostic ultrasound equipment, for example, will generally have a peak amplitude less than 3.0 MPa.

Both high and low acoustic pressure ultrasound systems generally operate within the frequency range of 20 KHz-10.0 MHz Interventional applications (such as in blood vessels) operate clinically up to about 50 MHz. Also ophthalmologic applications up to about 15 MHz. Diagnostic imaging typically uses frequencies of about 3 to about 10 MHz. Physical therapy ultrasound systems generally operate at frequencies of either 1.0 MHz or 3.3 MHz.

High acoustic pressure ultrasound or high intensity focused ultrasound has been used for tissue disruption, for example for direct tumor destruction. High intensity focused ultrasound using high acoustic pressure ultrasound is most commonly focused at a point in order to concentrate the energy from the generated acoustic waves in a relatively small focus of tissue.

Systems for permeabilization of target tissue cell membranes may employ either high acoustic pressure or low acoustic pressure ultrasound. Some embodiments may preferably employ relatively low acoustic pressure, for example the systems described herein where the transducers are mounted on the delivery devices and operate inside the body. Other systems may operate at interim acoustic pressure ranges. For example, systems described herein which employ an external ultrasound generator and transducer and which conduct the ultrasound to the target tissues through the use of a wave guide. In these systems, losses due to transduction through the wave guide can be compensated for by increasing the input power to the wave guide until adequate power is delivered to the target tissue. Finally, some systems described herein may employ focused or partially focused higher pressure ultrasound, for example the systems which employ an external mask to conduct the ultrasonic power through the tissues to the target tissues. It should be appreciated that combinations of high and low acoustic pressure systems may also be employed.

It should also be appreciated that any embodiment employing ultrasonic energy and ultrasound transducers can alternatively be configured as a microwave energy system using microwave antennas. For example, the embodiments disclosed herein relating to delivering energy from an external mask equipped with ultrasound transducers can also be configured to deliver microwave energy using one or more microwave antennas.

Figure 2B:
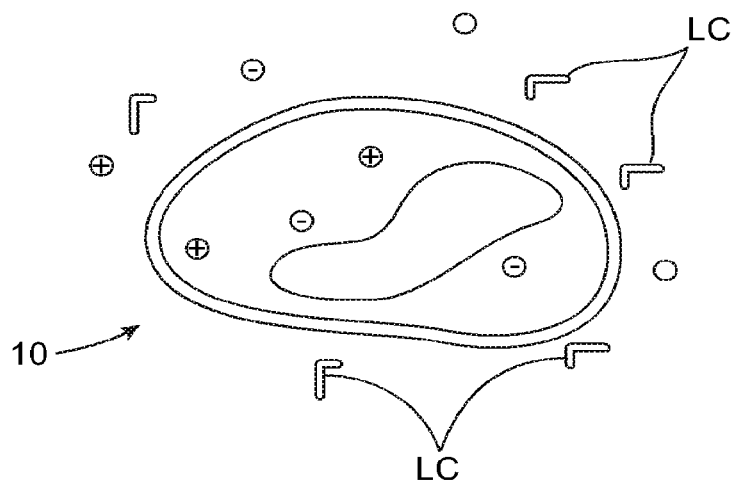
FIG. 2B—depicts a schematic of the target cell wherein LC molecule has been introduced.
Figure 3A:
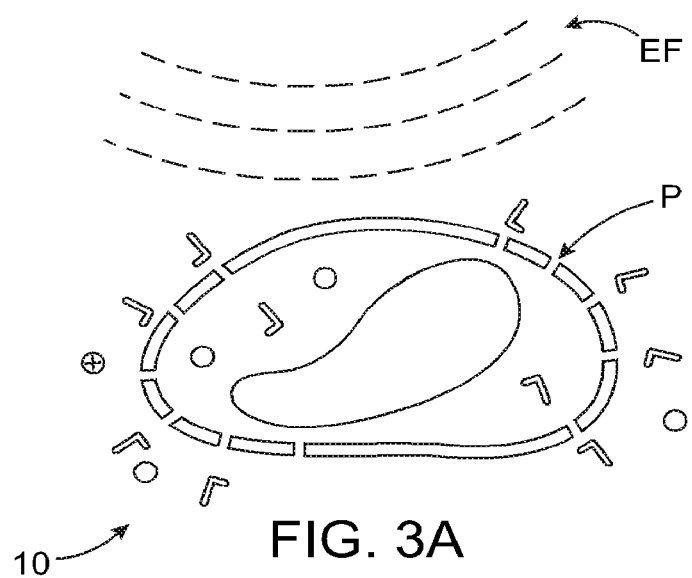
FIGS. 3A-3B—depicts a the target cell of FIG. 2 showing application of an energy field (EF) to produce permeabilization or pores (P) in the cell membrane, and introduction of the LC fragment therethrough.
Figure 3B:
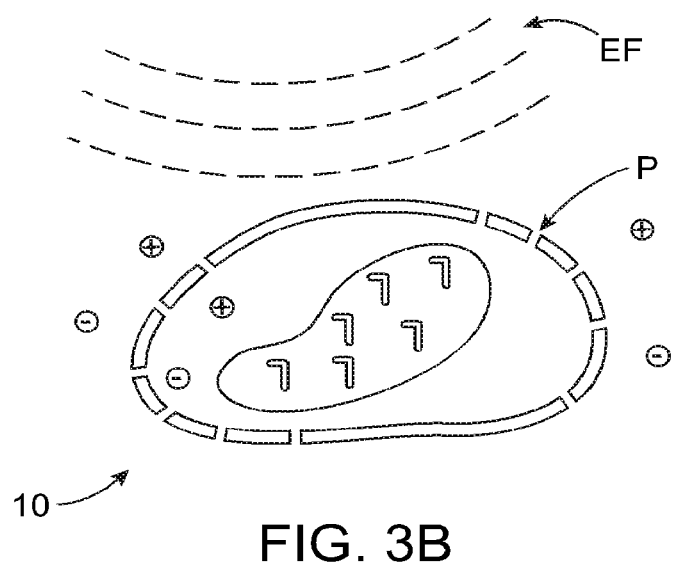
Figure 4:
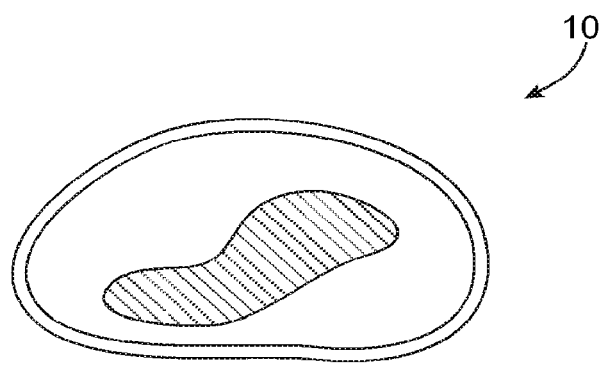
FIG. 4—depicts a schematic of a cell wherein the energy field has been discontinued, and neurotransmission of the cell has been effectively blocked.

A schematic example of the methods of the present invention are shown in FIGS. 2A, 2B, 3A, 3B and 4 in a simplified single cell model. A targeted cell, e.g., an epithelial or goblet cell of the type which line the nasal cavity membrane, is shown in FIG. 2A. Fragmented neurotoxin such as BoNT-LC (LC) is introduced into the vicinity of the targeted cell as depicted in FIG. 2B. An energy field (EF) is applied in accordance with the present invention resulting in the transfer of the BoNT-LC to the intracellular matrix (cytosol or cytoplasm) as shown in FIGS. 3A and 3B. Once this transfer has occurred, the release of acetylcholine from the presynaptic neurons at the neuromuscular junctions of the epithelial or goblet or other target cells is then blocked or disrupted. Once energy application is discontinued, the pores in the cell membrane recover or close as depicted in FIG. 4.

The terms "poration" and "permeablization" will also cover forms of cellular sonoporation. Just as pulses of high voltage electricity can open transient pores in the cell membrane, ultrasonic energy can do the same. See for example Guzman et al. "Equilibrium Loading of Cells with Macromolecules by Ultrasound: Effects of Molecular Sizing and Acoustic Energy", *Journal of Pharmaceutical Sciences,* 91:7, 1693-1701, which examines the viability of ultrasound to deliver molecules of a variety of sizes into target cells. In addition, techniques for nebulizing fluids and aqueous drugs are well known in the art, and as such, devices of the present invention may be adapted to introduce a BoNT-LC solution to a target region, such as the nasal passages and then effect selective membrane transport of the BoNT-LC into the cell using sonoporation.

To achieve the goals of the present invention, it may be desirable to employ methods and apparatus for achieving cell membrane permeabilization via the application of an energy source, either from a catheter located directly in the vicinity of the targeted cells, or an externally focused energy system. For purposes of this specification, the term "catheter" may be used to refer to an elongate element, hollow or solid, flexible or rigid and capable of percutaneous introduction to a body (either by itself, or through a separately created incision or puncture), such as a sheath, a trocar, a needle, a lead. Further descriptions of certain electroporation catheters are described in U.S. Provisional Patent Application No. 60/701,747 and Non-provisional patent application Ser. No. 11/459,582, the full disclosures of which are expressly incorporated herein by reference.

Figure 5:
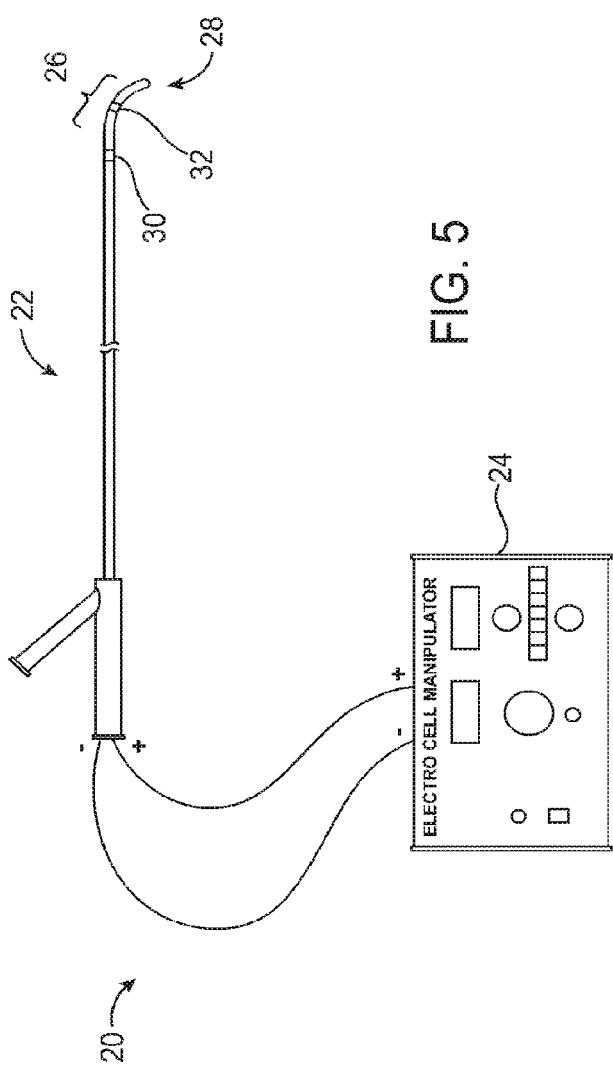
FIGS. 5, 5A-5B—depicts various embodiments of a delivery device of the present invention utilizing multiple energy transmission elements and an energy transmission system.
Figure 5A:
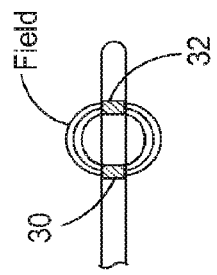
Figure 5B:

FIGS. 5 and 5A-5B depict a system utilizing an electroporation catheter for selective electroporation of targeted cells. In certain configurations of the present invention, voltages may be applied via the electroporation catheter to induce reversible electroporation at the same time as the catheter delivers the fragmented neurotoxin to the targeted region.

Referring to FIG. 5, electroporation catheter system 20 comprises a pulse generator 24 such as those generators available from Cytopulse Sciences, Inc. (Columbia, Md.) or the Gene Pulser Xcell (Bio-Rad, Inc.), or IGEA (Carpi, Italy), electrically connected to a catheter 22 having a proximal end and a distal region 26 adapted for minimally invasive insertion into the desired region of the body as described herein. The catheter further comprises an electroporation element 28 at the distal region thereof. The electroporation element consists for example of a first electrode 30 and a second electrode 32 operatively connected to the pulse generator for delivering the desired number, duration, amplitude and frequency of pulses to affect the targeted cells. These parameters can be modified either by the system or the user, depending on the location of the catheter within the body (intervening tissues or structures), and the timing and duration of reversible cell poration desired.

FIG. 5A depicts an arrangement of electrodes 30 and 32 that produces an electric field concentrated in a lateral direction from the catheter body whereas, FIG. 5B shows a device with electrodes 30 and 32 configured to create a more uniform electric field about the shaft of the catheter body. Further catheter device and electrode configurations are shown in FIGS. 6A-6D. FIG. 6A depicts an elongate catheter 40 having a first and second electrode (42 and 44) near the distal tip thereof, and including a monitoring or stimulation electrode 46 in the vicinity of the active porating electrodes for localizing the treatment area. In some embodiments, the monitoring or stimulating function may be performed by one or more of the treatment electrodes. The catheter device may have an optional sharp tip 48 to facilitate percutaneous introduction. FIG. 6B is a similar catheter device, but is further adapted to be steerable, or articulate at a region 53 near the distal end of the device. Such steering ability enables the operator to introduce the device into tight or tortuous spaces (such as the bronchial passages, or cardiovascular vessels) so that optimal placement of electrodes 52, 54 and 56 of the device at the target location may be achieved.

FIG. 6C depicts a further embodiment of the catheter device described above, that includes an injection element such as needle 62 to allow for the injection of a therapeutic agent such as a fragmented neurotoxin before, during or after the application of the pulsed energy or electroporation. The injection element may be a needle as shown in FIG. 6C, an infusion port, or other infusion means. Electrodes 64, 66 and 68 are provided as discussed with respect to FIGS. 6A and 6B.

FIG. 6D depicts an alternative embodiment of the present invention, showing a catheter device 70 having electrode elements (72 and 74) that are adapted to extend laterally from the main catheter body, and in some cases, penetrate the surrounding tissue prior to application of energy. In doing so the depth and direction of the energy field created by the electroporative process, may be further controlled. A reference electrode 76 may also be provided.

Figure 7:
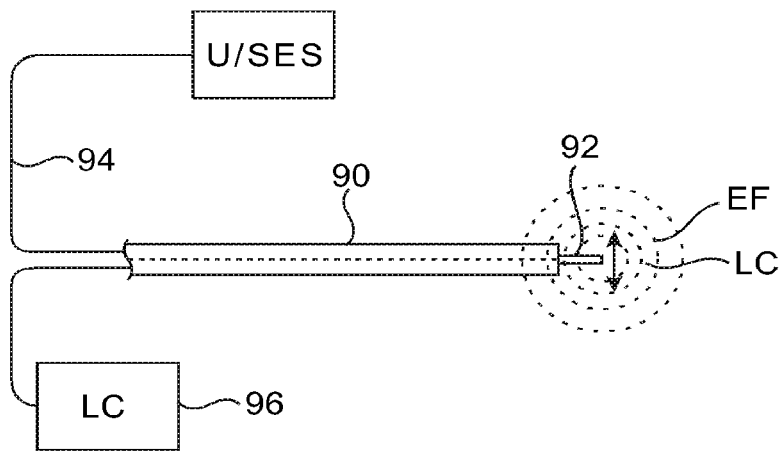
FIG. 7—depicts an embodiment of the present invention utilizing an ultrasound element on a catheter device.
Figure 8:
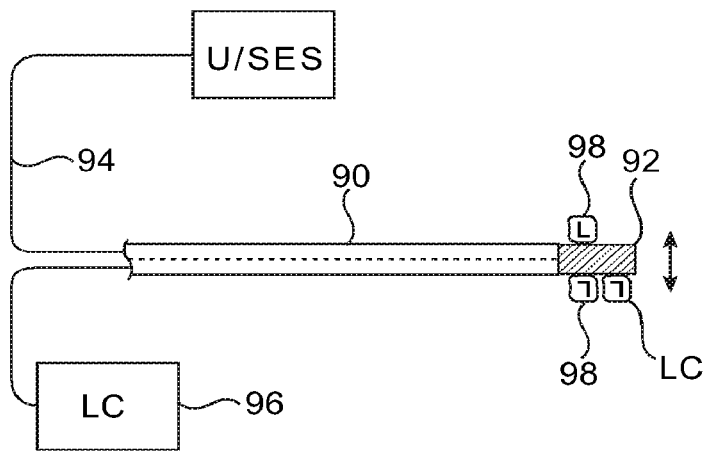
FIG. 8—depicts an embodiment of the present invention utilizing an aerosolizing element.

FIG. 7 depicts an embodiment of the present invention utilizing an ultrasonic element that may be particularly useful in delivery of the BoNT-LC to nasal tissue that provides a broad but targeted transport of the LC across the epithelial and goblet cell walls. In this device, ultrasound energy is delivered to the distal end 92 of the catheter device 90 via an ultrasonic waveguide that is operatively connected to an ultrasound energy source (U/SES) connected by cable 94. The LC fragment would be delivered from source 96 via the same lumen as the waveguide, or via a separate lumen that exits the distal tip of the device. In operation, the ultrasonic energy would cause the LC solution to be nebulized, forming mist clouds 98 within the lung, as shown in FIG. 8. The mist itself, in the appropriate concentrations, may act as an ultrasound coupler, conveying the ultrasonic energy to the wall of the lung or other targeted cellular structures, causing sonoporation of the targeted cells whereby the LC fragment is transmitted across the cell membranes to become an effective neurotransmitter blocker. In an alternative embodiment, an ultrasonic transducer may be located directly at the tip of the delivery device, eliminating the need for a wave guide. Various catheters useful for delivering vibrational energy to tissue are described in U.S. Pat. Nos. 6,361,554 and 6,464,680 to Brisken, the contents of which are expressly incorporated herein by reference in their entirety, for various therapeutic effects, such as enhancing cellular absorption of a substance.

Any of the catheter devices described herein, or described in the contemporaneously filed U.S. Provisional Patent Application No. 60/701,747 and Non-provisional patent application Ser. No. 11/459,582, previously incorporated by reference in their entirety, may be adapted to include an energy delivery element such as those described herein for purposes of providing a membrane transport system for delivery of a toxin fragment of neurotoxin. In addition, certain catheter devices and methods such as those set forth in U.S. Pat. Nos. 5,964,223 and 6,526,976 to Baran may be adapted to include energy transmission elements capable of producing a porative effect at the cellular level, including electrodes, ultrasonic elements and the like, for treatment in the nasal passages.

Furthermore, any of the foregoing systems may include electrodes or other monitoring systems either located on the treatment catheter, or external to the patient, to determine the degree of treatment to the region, including, thermocouple, ultrasound transducers, fiberoptics, sensing or stimulating electrodes. Further, it may be desirable to incorporate multiple pairs of electrodes that may be activated in pairs, in groups, or in a sequential manner in order to maximize the desired shape of the energy field (EF) while minimizing the field strength requirements.

Figure 9:
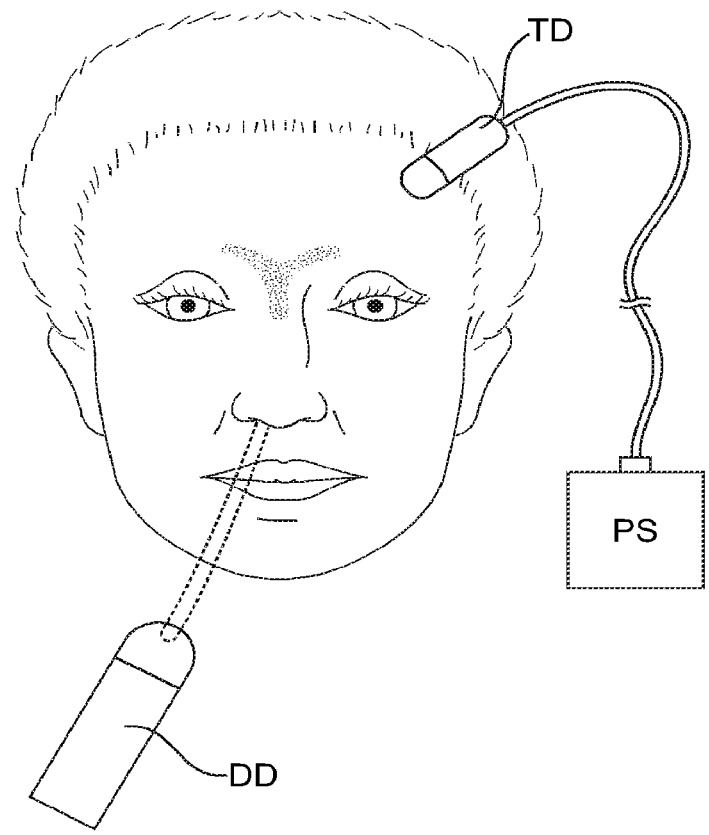
FIG. 9—depicts use on an external hand held transducer for enhancing cellular uptake of toxin delivered from a separate nasal aerosolizer.

It is within the scope of the present invention to deliver the toxin, the energy, or both, non-invasively. For example, as illustrated in FIG. 9, the patient may draw the toxin into the nasal cavity from a hand-held dispersion device DD. After a sufficient amount of the toxin has been infused into the nasal cavity, a separate hand-held transducer TD connected to an appropriate power supply PS will be energized and applied to the nasal cavities by passing the transducer over the appropriate regions of the forehead and nose. Optionally, the transducer can have a focused output so that the acoustic energy is focused in an appropriate depth beneath the skin surface. Typically, from about 0.1 cm to 2 cm.

Figure 10:
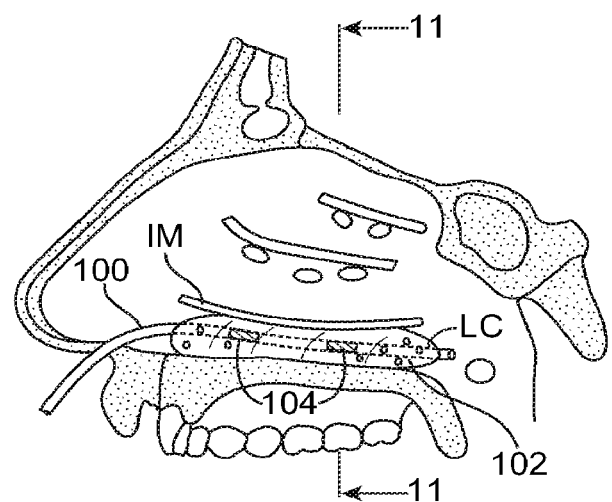
FIGS. 10 and 11—depicts depict use of balloon catheters for delivering toxin to the nasopharynx.

While the toxins and porating energy of the present invention may be delivered to the nasal cavity in a variety of ways, the following provides a number of specific examples of catheters and other structures for delivering toxins to preselected portions of the nasal cavity. For example, as shown in FIG. 10, a balloon catheter 100 may be provided with a porous balloon 102 at its distal end. The balloon would be porous over at least a portion of its body so that solution delivered to inflate the balloon, which would contain desired levels of the toxin or toxin fragment, would release the solution through the balloon at a controlled rate. By further providing one or more ultrasonic transducers 104 within the balloon, optionally mounted on the catheter body, ultrasonic poration energy can be delivered to the adjacent nasal membranes which are receiving the toxin solution. As illustrated in FIG. 10, the toxin is being delivered to a lower surface of the inferior meatus IM to localize and enhance cellular delivery at the balloon tissue interface. Alternatively, the balloon could carry the toxin in a releasable form over its exterior surface in order to deliver to any adjacent tissue structure. In some instances, the toxin could be carried or encapsulated in delivery vesicles which are preferentially fractured by the same acoustic energy which permeablizes the cell wall. Other coatings include hydrogels, such as those produced by Surmodics, Inc., BioCoat, Inc., or the like. In some instances, it may be desirable to provide a coupling agent over and/or within the balloon in order to enhance the delivery of ultrasonic energy from the internal transducer. In still other instances, it would be possible to place polymeric transducers on or within the balloon surface in order to directly deliver ultrasonic or other acoustic energy into the adjacent tissues.

In all the above cases, the ultrasonic transducers can be configured in order to selectively deliver the energy to desired portions of the adjacent tissues. For example, in the embodiment of FIG. 10, the internal transducers 104 can be configured to focus the ultrasonic energy generally upwardly (as viewed in FIG. 10) in order to preferentially deliver the toxins into the inferior meatus IM while minimizing delivery elsewhere.

As a further option, the balloon could be inflated by a coupling agent in order to enhance the transmission of the ultrasonic or other acoustic energy, while the toxin solution could be infused into the treatment area before or simultaneously using either a separate lumen in the catheter or a separate tube or other delivery catheter. In this way, it would not be necessary to inflate the balloon with a relatively large volume of the toxin solution.

The balloon catheters can be introduced by any conventional technique, for example, in some instances, it may be desirable to use a guidewire to place the catheter into a desired sinus or other location, optionally using fluoroscopic, MM or ultrasound imaging.

Figure 11:
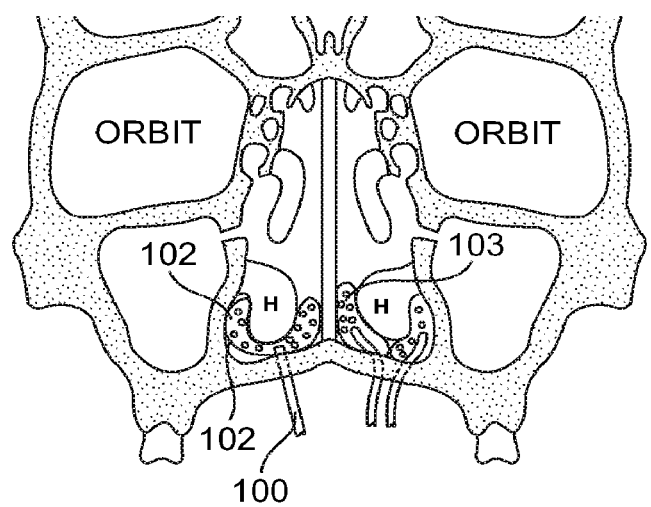

Referring now to FIG. 11, a front view of particular balloons placed as generally shown in FIG. 10, is shown in more detail. A single balloon 102 can be around the structures H in the inferior meatus. Alternatively, a pair of balloon structures 103 may be placed in the same space, as shown in the right hand portion of FIG. 11. Optionally, the balloons could be formed from an elastic material, such as a silicone, urethane, latex, thermoplastic elastomers, or other materials where the material is treated to be appropriately porous, for example by laser drilling. Alternatively, the balloons could be formed from non-distensible materials which are pre-formed to conform to the desired target cavities. The non-distensible balloons could also be laser drilled or otherwise made permeable in order to release the toxin solutions of the present invention. Alternatively, either type of balloon could be coated with the toxin solutions, coupling solutions, or other materials which are useful in the protocols of the present invention.

Figure 12A:
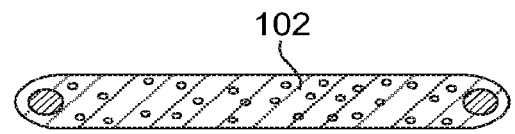
FIGS. 12A-12C—depict use of a self-expanding toxin delivery structure on a catheter.
Figure 12B:
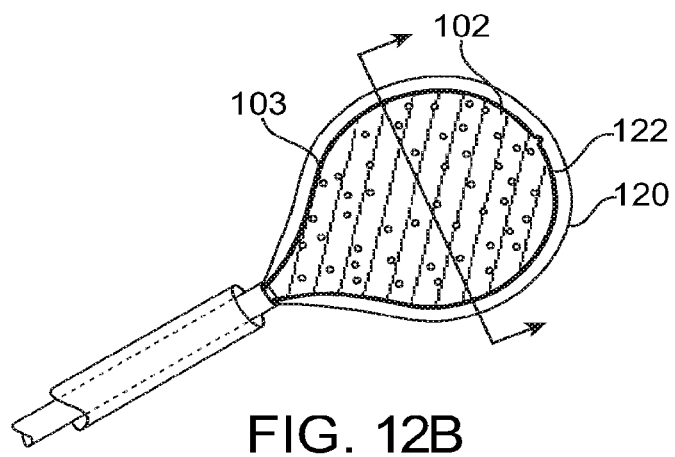
Figure 12C:
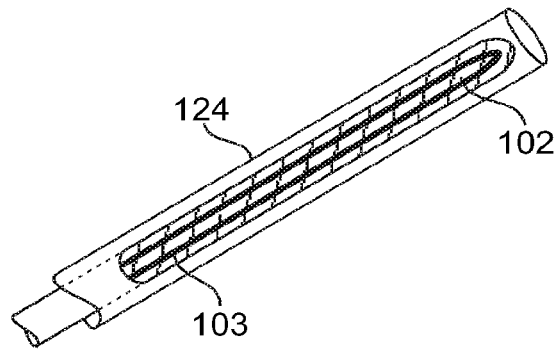

Referring now to FIGS. 12A. 12B, and 12C, as an alternative to inflatable balloons, toxin delivery structures may be made to be various shapes, for example a generally "flattened" balloons 102, whose profile is narrower in one axis than the other, for example by placement of an internal nitinol or other elastic frame or scaffold, or a stainless steel wire 103 that is fed into the balloon outer structure to form such shape, within a suitable porous cover or membrane. Thus, the structure 120 may be expanded by the scaffold 122 after release from a delivery tube 124. The structures can be used to deliver energy and/or toxin in any of the ways described previously with respect to balloons, including by carrying a transducer or electrode on or within the structure and delivering a toxin solution from the interior of the self-expanding structure through a porous portion of the structure wall.

Figure 13:
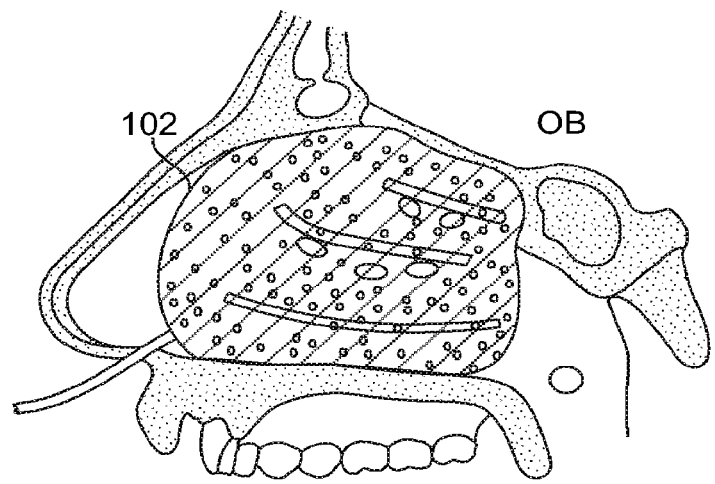
FIGS. 13 and 14—depict a protocol for limiting toxin introduction by partial filling of a porous delivery balloon.
Figure 14:
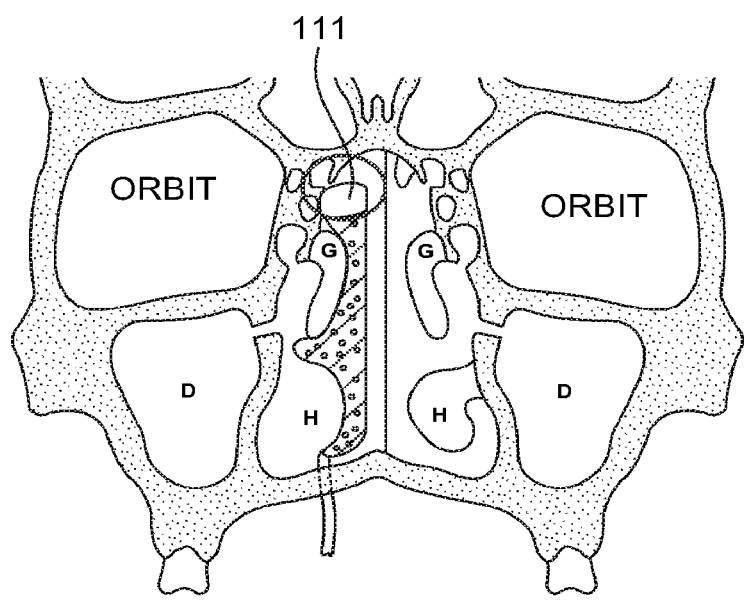

In some instances, it will be desirable to protect the olfactory bulb of the sinuses from treatment with the toxin solutions of the present invention. Referring now to FIGS. 13 and 14, the porous portion of a delivery balloon 102 can be positioned so that the remaining non-porous segment is in contact with the olfactory bulb (FIG. 13). Thus, when the balloon is inflated and the toxin solution delivered, it will not be directed at the tissues of the olfactory bulb (OB).

As shown in FIG. 14, which is a cross-sectional view of FIG. 13, instead of rendering the top portion of the delivery balloon non-porous, it would be possible to simply refrain from filling the top portion with the toxin solution and/or a coupling solution. This can be achieved by filling the balloon with a known volume of air 111 in addition to the toxin solution. With the patient positioned appropriately, the air will fill the portion of the balloon in proximity to the olfactory bulb, excluding this tissue from toxin contact. Additionally, the air bubble may act as an ultrasound insulator to inhibit energy delivery to the non-targeted or protected tissue. Thus, delivery of the toxin to the region around the olfactory bulb and/or delivery of the energy to the region around the olfactory bulb can be partially or wholly prevented.

Figure 15:
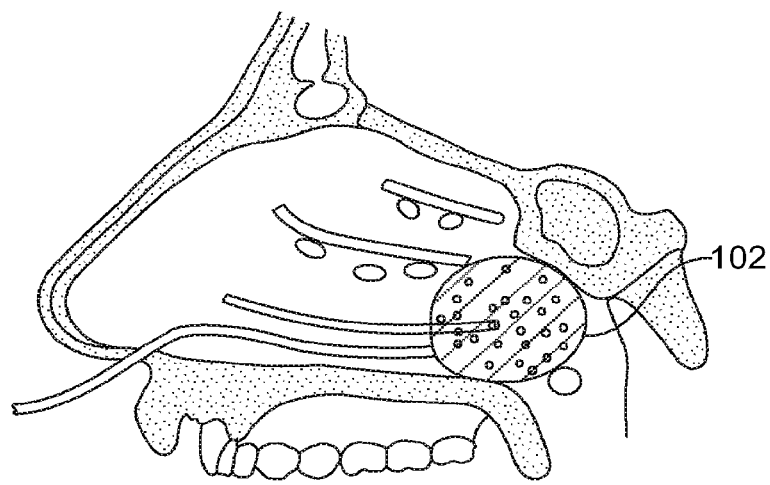
FIG. 15—depicts sizing of a delivery balloon to control distribution of toxin released into the nasal cavity.
Figure 16:
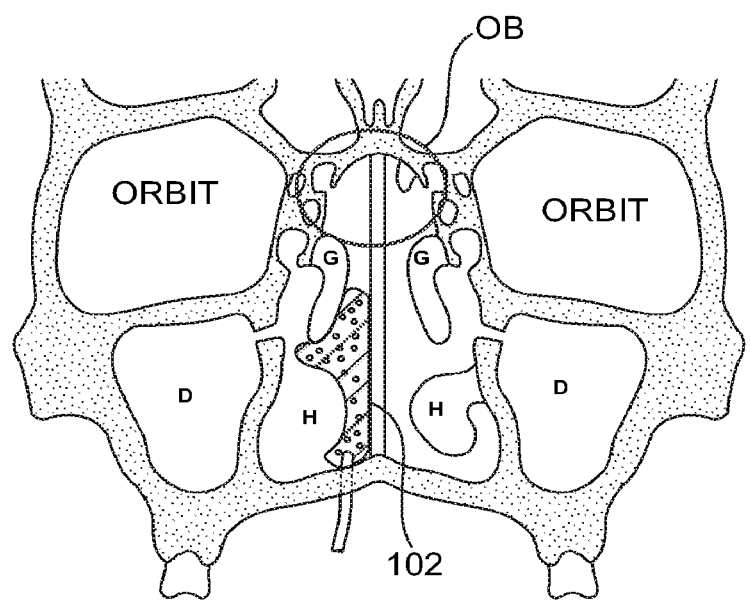
FIG. 16—depicts placement of a delivery balloon to protect the olfactory bulb.

Referring now to FIGS. 15 and 16, the balloon may be sized and positioned to target an area of high epithelial or goblet cell (G) concentration, for example in the back of the nasal passages in the area of the nasopharynx. By targeting this area of the nasal membrane, a high percentage of mucus-secreting epithelial or goblet cells can be treated with a device which is relatively small and which may carry a relatively low infusion volume and require less energy. Moreover, the olfactory bulb is inherently protected with this technique since the balloon is positioned well away from that area. If desired, of course, additional shielding, shaping or other protective balloons could be positioned between the olfactory bulb and the toxin and energy delivering components of the present invention.

Figure 17:
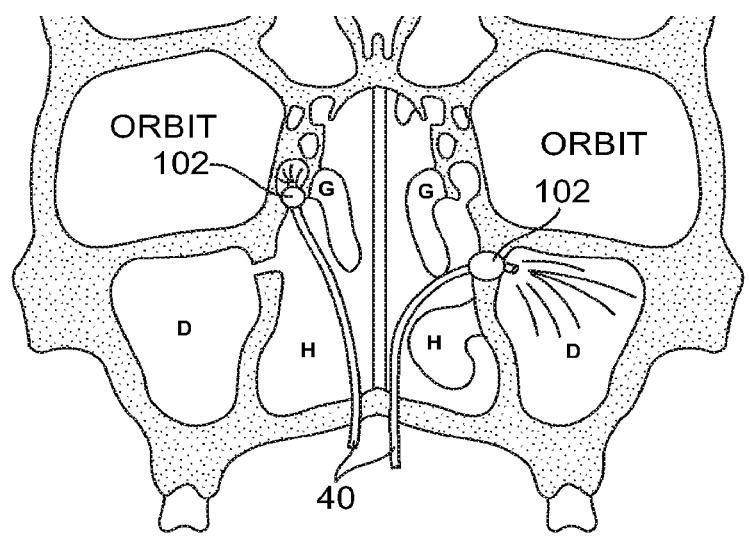
FIG. 17—depicts the use of multiple small balloons for selective toxin delivery into the nasal cavity.

As shown in FIG. 17, direct infusion and treatment of particular sinuses may be effected using relatively small occlusion balloons 102 which occlude and isolate natural openings into those sinuses. Once the balloon is in place and the occlusion balloon employed, the toxic solution can be delivered by infusion, dispersion, or other conventional techniques. Once the toxin solution is present in the sinus, all or a portion of the membrane of the sinus can then be treated with an external or other ultrasonic source.

Figure 18:
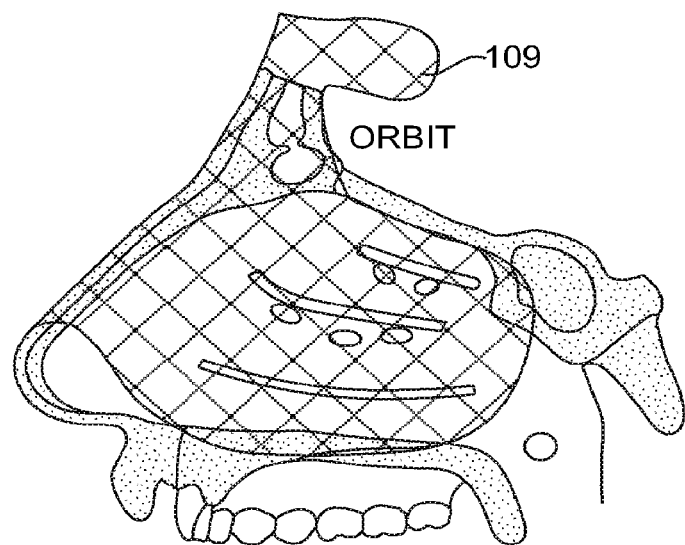
FIG. 18—depicts sonoporation using an external mask placed over the sinuses and nose.
Figure 19:
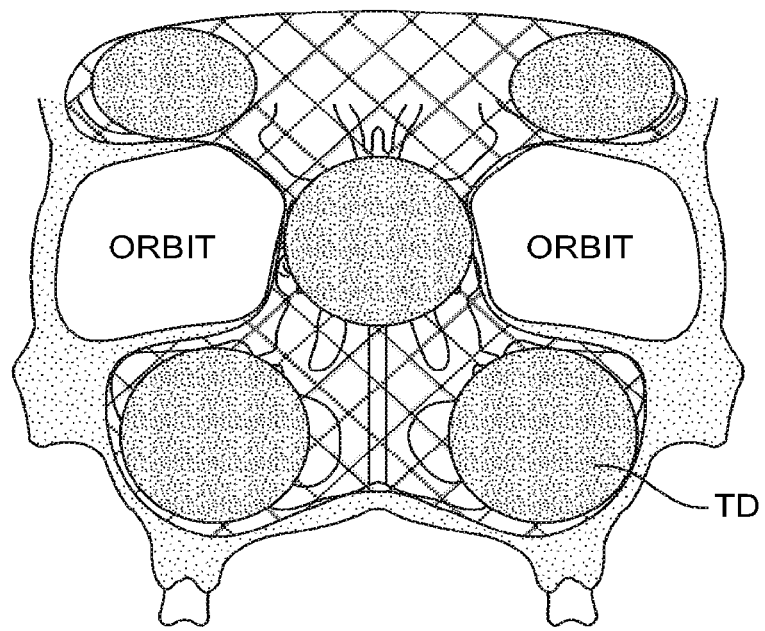
FIG. 19—depicts a front view of an external sonoporation mask showing placement of ultrasound transducers.

For example, as shown in FIGS. 18 and 19, the external transducer may comprise a mask which conforms to the nose and optionally over the sinuses, where the mask carries one or more ultrasonic or other acoustic transducers (TD) adapted to deliver energy transcutaneously into the sinuses. The mask may comprise a plurality of individual transducers (TD), which may be made from one, two, or several generally continuous piezoelectric films which are formed over or lamented within the mask. Alternatively, multiple individual piezoelectric crystal transducers can be built into the mask.

The effect of such externally applied ultrasonic energy can be enhanced by introducing microbubbles (free air) into the isolated sinuses and/or nasal passages which have been filled with toxin solution. For example, encapsulated microbubbles, which are generally useful as echocardiographic contrast agents, or specialty perfluorocarbons, are useful as such ultrasonic enhancing agents. By encapsulating the toxin molecules in spheres or bubbles, or by simply placing the spheres or bubbles in proximity to toxin molecules, the ultrasonic or other acoustic energy can be captured and stored until it is abruptly released with fracture of the sphere or bubble. Such microspheres will also act as resonance bodies as defined below.

Figure 20:
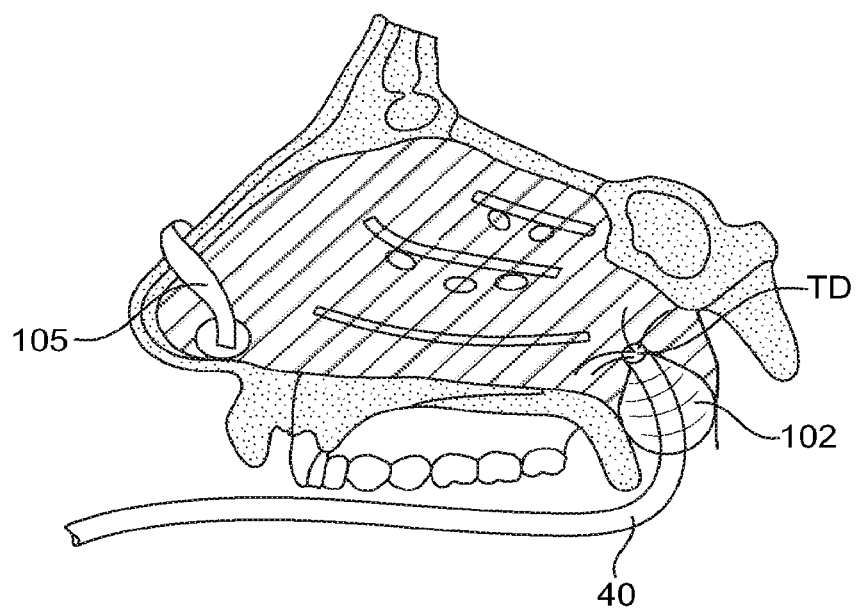
FIGS. 20 and 21—depict an orally-introduced occlusion catheter and energy applicator system.
Figure 21:
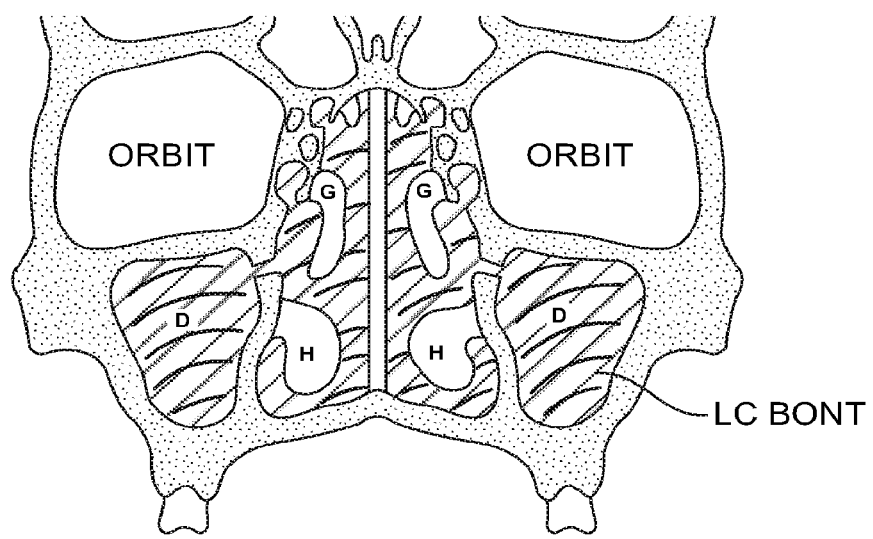

Referring now to FIGS. 20 and 21, a catheter 40 is placed at the posterior outlet of the nasal passages in the region of the nasopharynx. The catheters configured to occlude outflow from these sinuses and passages into the throat. As shown in FIG. 20, a balloon catheter 102 or other occlusion device could be configured to block such passage. As shown in FIG. 20, the catheter is delivered in through the mouth and guided into the posterior portion of the nasal cavities, typically using a guidewire. Once the nasopharynx of the posterior portion of the nasal cavity is occluded, toxin solution (BoNT) can be infused through the occluding catheter lumen, or through a separate infusion catheter or tube, in order to treat substantially the entire sinus and/or nasal cavity membrane at once (FIG. 21). When the toxin solution is introduced through the catheter at the posterior region of the cavities, it will frequently be desirable to occlude the nostrils, for example using a nasal clip 105.

Figure 22:
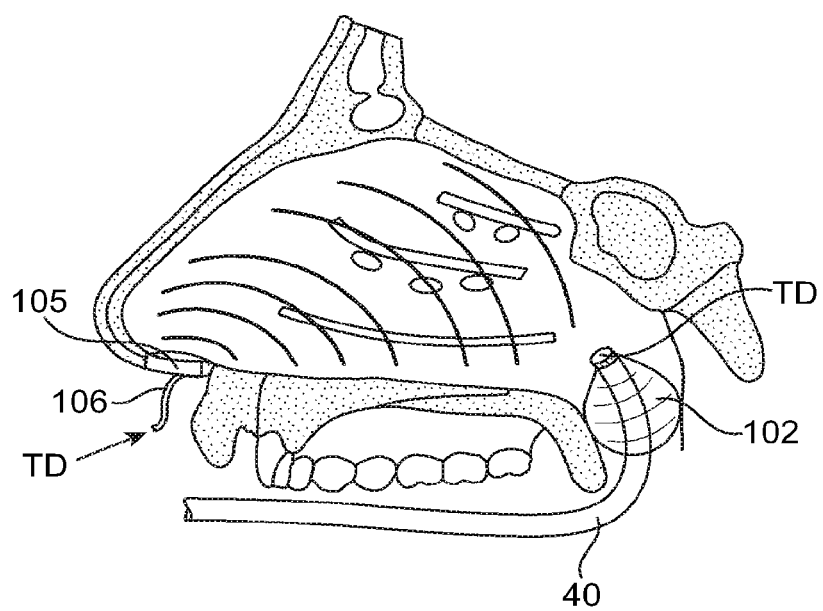
FIGS. 22 and 23—depict nose plugs for occluding and optionally delivery poration energy to the nasal cavity.
Figure 23:
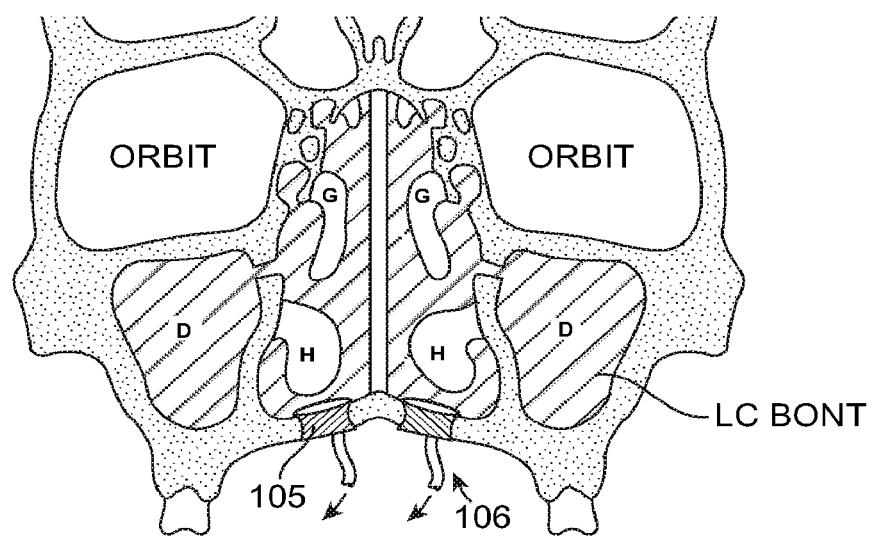

As shown in FIGS. 22 and 23, specially designed nose plugs 105 can be provided with air bleed valves 106 which are used to occlude the nostrils in order to evacuate or bleed air from the nasal passages while filling the passages with the toxin solution. The nose plugs 105 could optionally include ultrasonic transducers in order to deliver ultrasonic or other acoustic energy into the solutions entrapped within the nasal cavities using the nostril plugs. Alternatively, of course, the ultrasound or other acoustic energy could be delivered from an external transducer as described previously.

Figure 24:
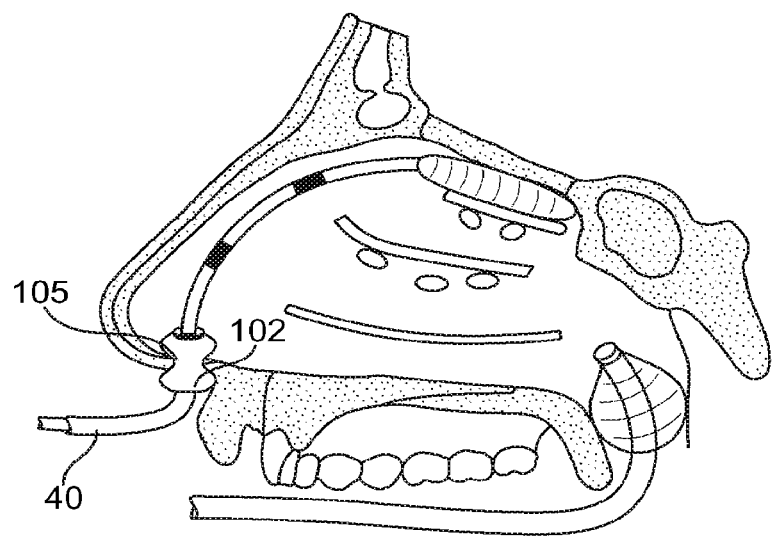
FIGS. 24 and 25—depict an alternate occlusion catheter system for targeted toxin delivery to the nasopharynx.
Figure 25:
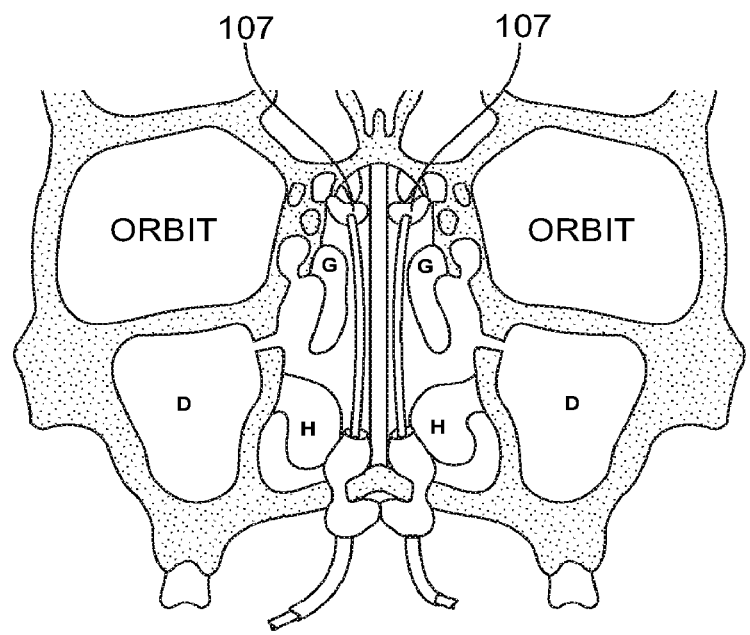

Referring now to FIGS. 24 and 25, an alternate occlusion catheter system for nasopharynx occlusion is illustrated. An occlusion catheter 40 is introduced through a nostril, where the tip includes an ultrasonic transducer to provide sonoporation. A nostril plug 105 is provided proximally on the shaft of the catheter, while the cavity is blocked with a separate occlusion balloon 102 introduced through the mouth and into the posterior nasopharynx region. The toxin solution can be introduced into the cavity through either the catheters which pass through or reside in the nostrils or the catheter which occludes the posterior nasopharynx.

Figure 26:
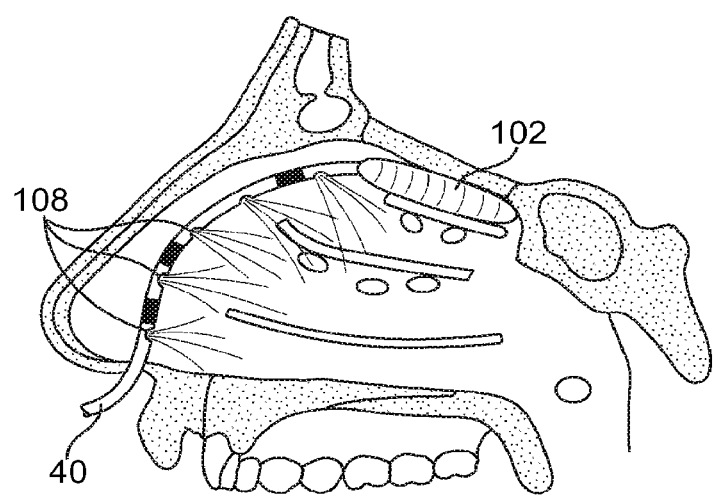
FIGS. 26 and 27—depict use of a toxin delivery catheter having side holes and a distal occlusion balloon for isolating and protecting the olefactory bulb.
Figure 27:
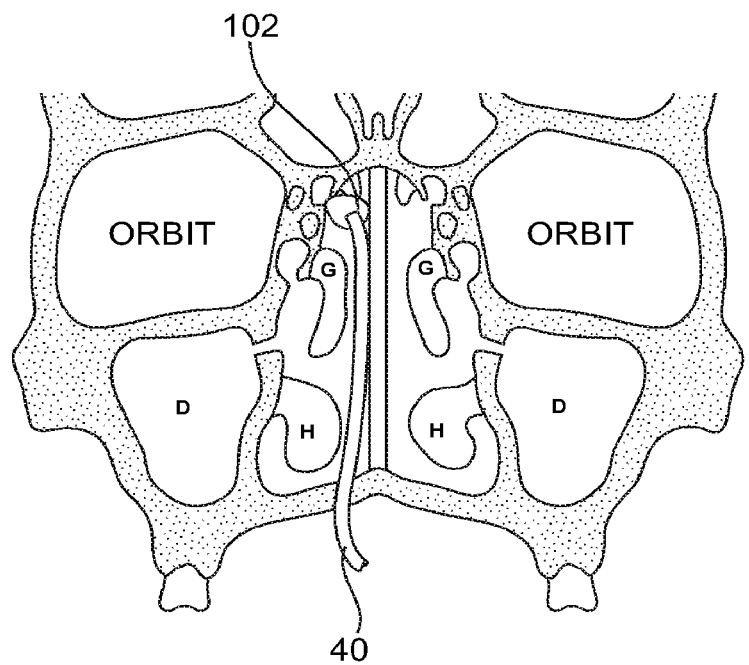

FIGS. 26 and 27 illustrate how a catheter 40 with side holes 108 can be configured to deliver toxin away from the olfactory bulb, even when used alone without separate nasopharynx occlusion catheters. The catheters preferably carry an occlusion balloon or other structure near their distal ends 107 to prevent or inhibit toxin from reaching the olefactory bulb Use of these or other catheter devices can deliver toxin incorporated into vesicles which may be configured as "resonance" bodies, which reduce the need to fill the nasal cavities with a liquid or other form of toxin. For example, lipid microspheres which incorporate the toxin may be sprayed or aerosolized onto target surfaces of the nasal epithelium. After the lipid or other resonance bodies are attached to the targeted epithelium membrane surface(s), the ultrasound energy can be delivered from the catheter or externally through the skin in order to selectively porate the epithelial or goblet cells to enhance introduction of the toxin vis-à-vis resonance bodies. A protection device at the end of the shaft can be provided to shield the olfactory bulb from the toxin.

Figure 29:
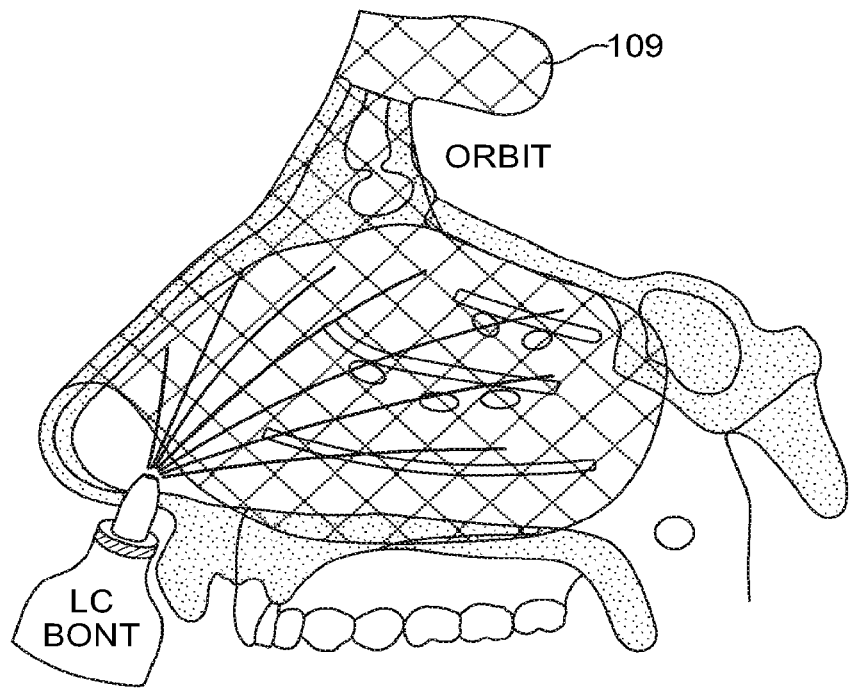
FIG. 29—depicts toxin delivery using a nasal spray and energy delivery using a face mask.

Referring to FIG. 29, the toxin may be delivered as a conventional nasal spray (BoNT), as mentioned hereinbefore, and the poration energy can be delivered through a face mask. The poration energy might alternatively be delivered as ultrasound energy delivered through a mist, without direct contact to the tissues. This mist might be the same mist which contains the toxin, or it might be a different, possibly denser mist delivered at some time after the toxin has been delivered. The delivery devices for these mists might be introduced a relatively short distance into the nose. Thus the entire therapy might comprise the specialized delivery of two mists.

Figure 28:
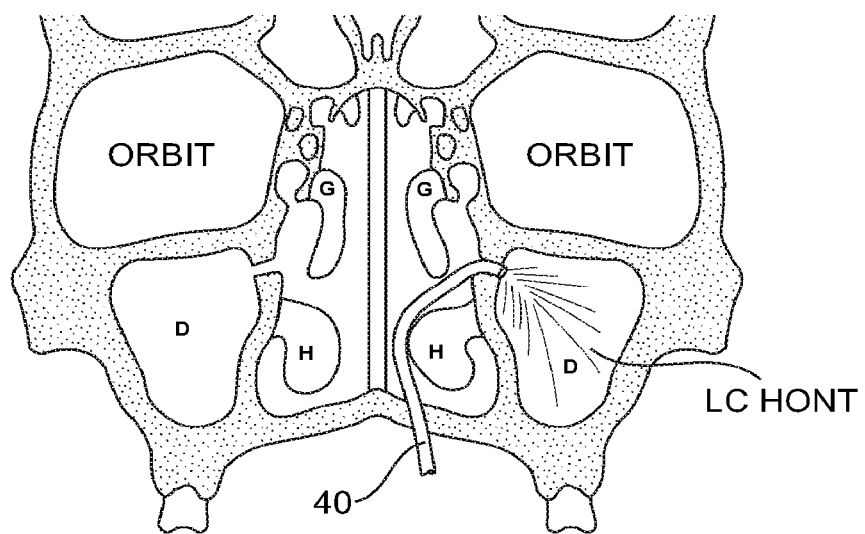
FIGS. 28 and 30—depict use of a simple catheter having a shaped distal end for aerosolizing a toxin into a target nasal sinus though an ostium open to the sinus.
Figure 30:
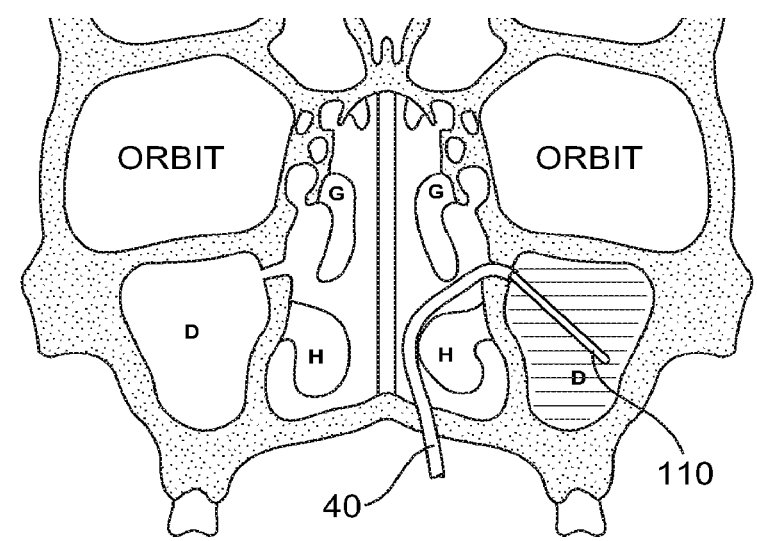

Referring now to FIGS. 28 and 30, an infusion catheter 40 can be engaged against the ostium of a sinus cavity (FIG. 28). A guidewire 110 may then be advanced through the infusion catheter and into the sinus cavity (FIG. 30). The guidewire can be formed as a wave guide to deliver ultrasonic energy, as an electrode to deliver electroporation energy, or as an infusion wire to deliver the toxin solution itself. The wire could further be configured to perform two or more of these functions. The catheter could be configured to act as a counter electrode when the guidewire is acting as an electroporation electrode in bipolar energy delivery.

Figure 31:
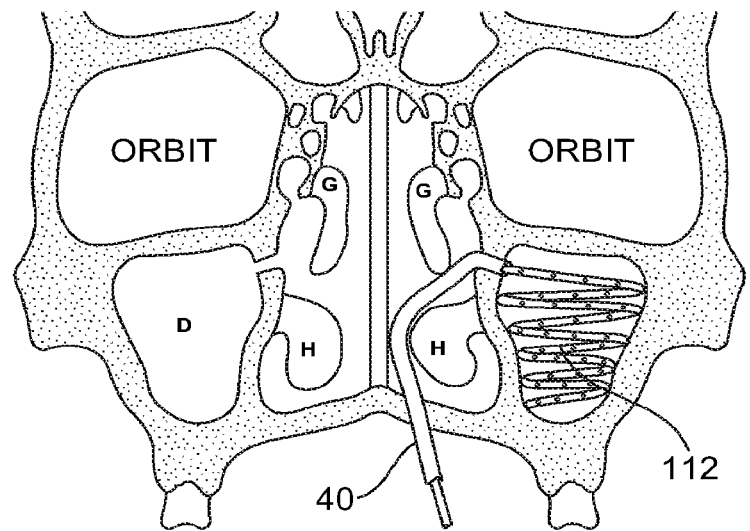
FIGS. 31 and 32, depict use of a catheter having a shaped distal end for positioning separate infusion structures with a target sinus cavity.

Referring now to FIG. 31, the catheter advanced to the os of a sinus cavity, as illustrated, can also be used to deliver a helical or randomly shaped delivery tube 112 which is deployed within the sinus. Preferably, the tube will expand to engage a major portion of the wall of the sinus cavity. Alternatively, the geometry could be selected to selectively engage only a particular portion of the wall of the sinus cavity. The wire can further be adapted to deliver energy, either electrical or acoustic, and/or may be configured to deliver and distribute the toxin solution within the cavity. In still other configurations, the wire could be coated to deliver the agent to the wall, and still further the wire could deliver ultrasound gels, saline, degassed water, or the like, to enhance coupling of a separate ultrasonic energy source.

Figure 32:
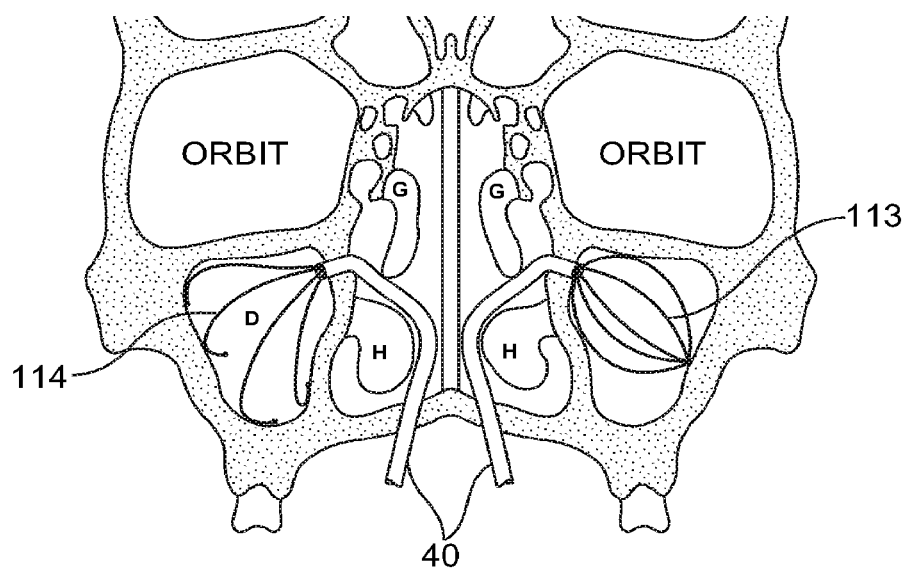

Referring now to FIG. 32, two or more deployment catheters can be used to advance any of the guidewires or other wire structures discussed above. As illustrated in FIG. 32, an electrode basket 113 may be deployed through the delivery catheter. Alternatively, a multiply tined catheter 114 structure may be delivered through the delivery catheter.

Figure 33:
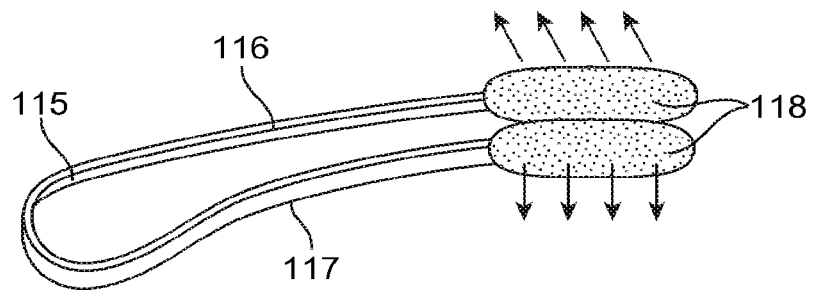
FIG. 33—depicts an applicator device for delivering toxin to the nasal cavity having a handle and two applicator tips for placement within the nasal passageway.
Figure 34:
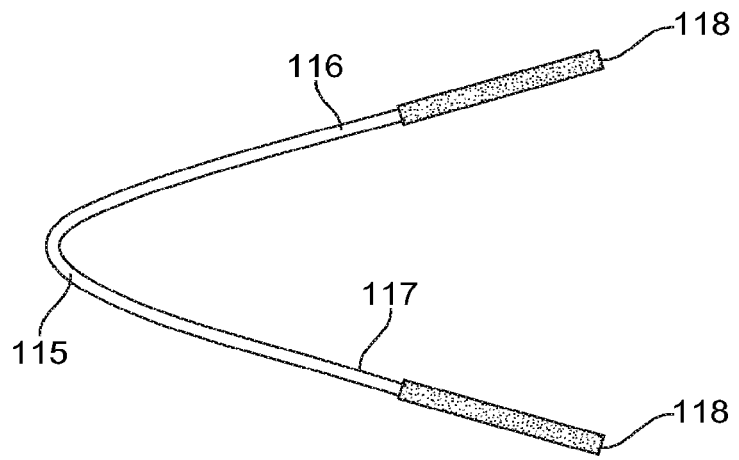
FIG. 34—depicts a top view of the applicator device illustrated in FIG. 33.
Figure 35:
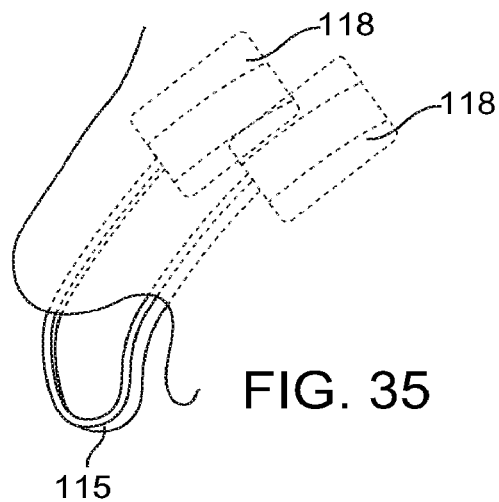
FIG. 35—depicts the applicator device illustrated in FIG. 33 when placed within the nasal passageway.

FIGS. 33 and 34 illustrate a device for applying BoNT to the treatment area within the nasal cavity. This device comprises a handle 115 having a proximal section, a body and a distal section. The body of the handle comprises a first member 116 and a second member 117. The first member and second member merge at the proximal section and terminate at the distal section, wherein the distal section comprises a first end and second end corresponding to the first member and second member. The device further comprises applicator tips 118 connected to each of the first end and second, wherein the applicator tips are configured for insertion into the nasal passageway, as shown in FIG. 35.

Figure 36:
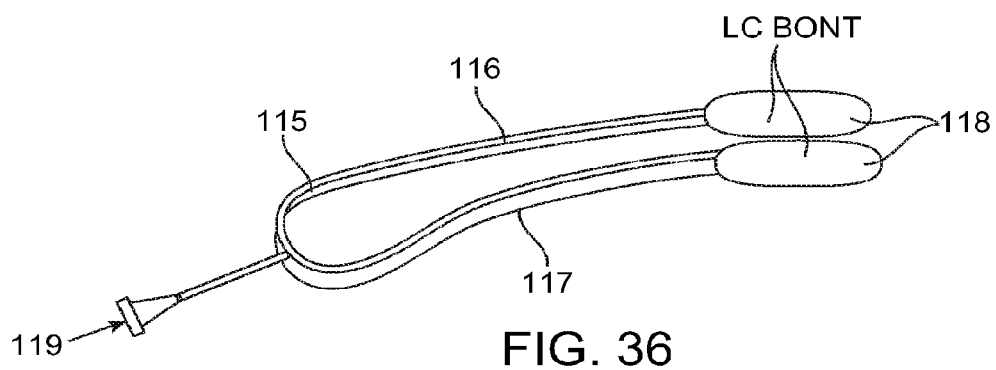
FIG. 36—depicts an applicator device configured with an infusion channel and access port for infusing solution to the applicator tip.

Once within the nasal cavity, the applicator tips 117 and 118 can apply BoNT to the nasal passageway and, specifically, the turbinates along the nasal wall. The BoNT can be applied or affixed to the applicator tips as a liquid solution, gel, foam, cream, lotion and/or a lyophilized compound prior to being positioned within the nasal passageway. Alternatively, as illustrated in FIG. 36, the handle can be configured with an infusion channel 119 for delivering the BoNT to the applicator tips following placement in the nasal passageway. In this configuration, the handle may further comprise an access port at its proximal section that is in fluid communication with a BoNT source.

Figure 37A:
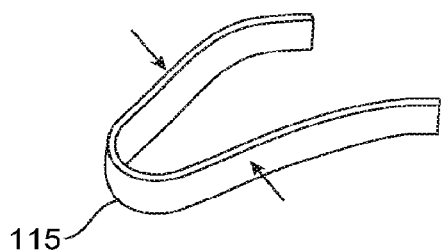
FIGS. 37A-37C—depict the handle of an applicator device in an isometric view, a top view in an expanded state and a top view in a compressed state, respectively.
Figure 37B:
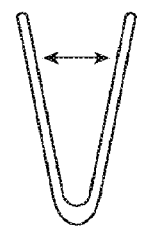
Figure 37C:
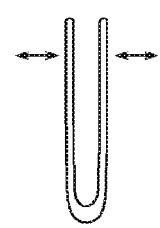

As shown in FIG. 33, the loop member may be configured to provide an outward lateral force such that the applicator tips 118 are firmly contacted against the nasal turbinates when placed in the nasal passageway. With reference to FIG. 37A, the operator would apply inward pressure in the direction of the arrows to the handle to achieve a compressed configuration, as shown in FIG. 37C, prior to inserting the applicator tips into the nose. Once the applicator tips of the device are properly inserted into the nasal passageway, this pressure would be released such that the outward bias in the handle transitions the handle from a compressed configuration to an expanded configuration, as shown in FIG. 37B, wherein the applicator tips are pressed against the nasal turbinates. The applicator tips can be held against the turbinates by the outward bias for sufficient time to allow a therapeutically effective amount of BoNT to be absorbed by the nasal cavity wall.

Figure 38:
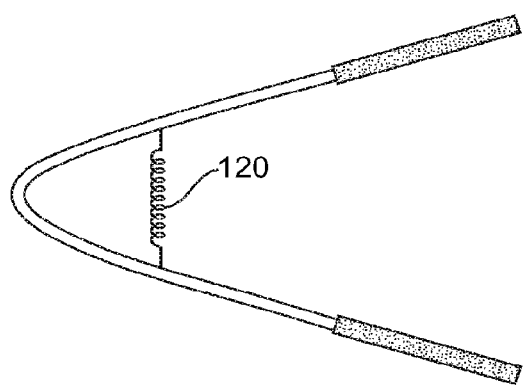
FIG. 38—depicts an applicator device comprising a spring element.

This outward bias may be achieved by spring loading the device 120. Specifically, the handle itself may comprise a spring element, wherein the handle is dimensioned and configured with a residual spring force that exhibits this outward bias. Additionally or alternatively, the handle may comprise a material with mechanical properties to facilitate the spring action with little to no inelastic deformation resulting from the inward pressure applied by the operator. For example, at least a portion of the proximal section of the handle may comprise spring steel, stainless steel, nitinol, or MP35N alloy. Alternatively, as illustrated in FIG. 38, a spring element 120 that is separate from the handle may be used to apply outward lateral pressure to the first and second members of the handle body.

To facilitate the insertion of the tip applicator through the nostril and into the nasal passageway, it may be desirable for the applicator tip to initially have a low volume configuration. Once properly positioned in the nasal passageway, it would be desirable for the applicator to have an expanded volume configuration for maximizing contact with the nasal turbinates. In one exemplary embodiment, the tip applicator may comprise a sponge such that the sponge 121 is in a low volume configuration when dry (FIG. 39A) and an expanded configuration when wet (FIG. 39B), wherein the sponge 121 is configured to fit securely within the nasal passageway.

Figure 39A:
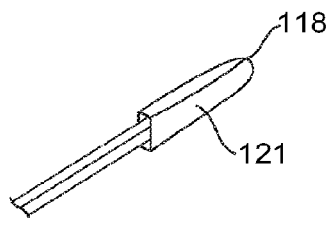
FIGS. 39A-39B—depict a sponge applicator tip for an applicator device in a dry low volume configuration and a wet expanded configuration, respectively.
Figure 39B:
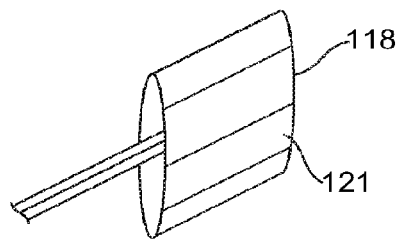

In the embodiment illustrated in FIGS. 39A and 39B, the dry sponge applicator could be preloaded with lyophilized BoNT and wetted with a liquid (e.g., saline) following placement of the applicator in the nasal passageway. The liquid can be introduced into the nasal passageway using a spray or a catheter, or the BoNT may simply be rewetted by the nasal secretions themselves. Alternatively, as described with respect to FIG. 36, the liquid can be infused into the applicator tip through a channel 119 in the device handle. Still alternatively, the liquid infused through the channel can be a solution comprising BoNT, thereby eliminating the need for the dry sponge applicator to be preloaded with BoNT.

Figure 40A:
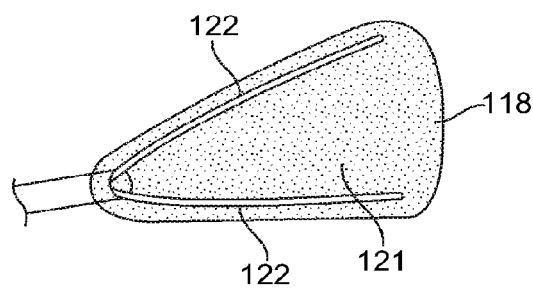
FIGS. 40A-40B—depict an applicator tip comprising a spring element in an expanded configuration and a compressed configuration, respectively.
Figure 40B:
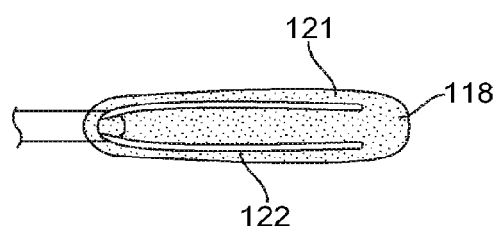

To facilitate the expansion of the applicator tip, thereby maximizing the surface contact between the nasal cavity wall and applicator tip, it may be desirable to incorporate a spring element 122 within the applicator tip 118. The embodiment in FIGS. 40A and 40B shows an applicator tip comprising a sponge 121 and a spring element 122 in an expanded and compressed configuration. This configuration can be used instead of or in addition to the wet/dry sponge embodiment discussed above.

Figure 41:
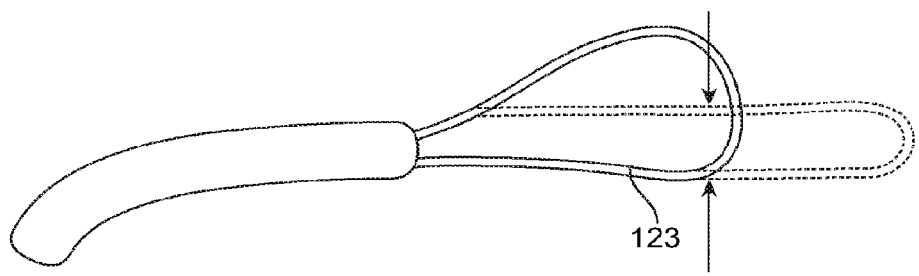
FIG. 41—depicts an applicator device comprising loop spring element.

The spring element may comprise any type of compressible spring and any number of elastically deformable polymers or metals, including, spring steel, stainless steel, nitinol, and MP35N alloy. As shown in many of the above embodiments, the spring element may comprise a v-shape spring. Alternatively, the spring element may comprise a closed-loop spring 123, as illustrated in FIG. 41.

For embodiments utilizing a spring-loaded applicator tip, it will be necessary to hold the spring 122 in its compressed state until it is properly positioned within the nasal cavity, at which time the spring can be released to allow the applicator to expand into the nasal cavity. In the wet/dry sponge 121 embodiment described with respect to FIGS. 39A and 39B, a sponge and spring can be selected and matched such that the stiffness of the dry sponge is sufficient to overcome the spring stiffness and hold the spring in a compressed configuration until it becomes wet.

Figure 42:
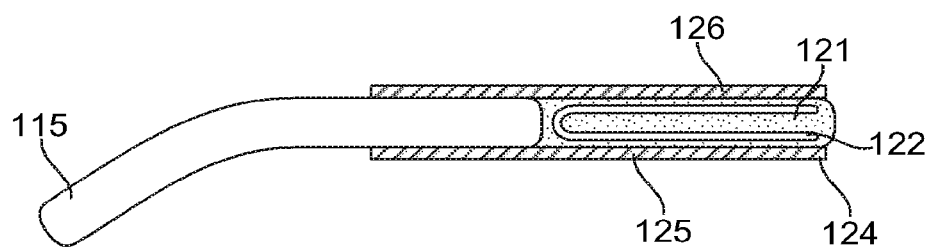
FIG. 42—depicts a spring-loaded applicator tip held in a compressed state by an engaged actuator.

In another embodiment employing a spring-loaded applicator tip, an actuator can be used to hold the spring in a compressed state. FIG. 42 illustrates a spring-loaded applicator tip 124 that is restrained in a compressed state by a slidably-engaged actuator 125. The slidably-engaged actuator may comprise a retractable sheath or collar 126 for holding the spring in its compressed configuration. Once the applicator is positioned within the nasal cavity, the actuator can be retracted to release the spring, thereby expanding the applicator.

Figure 43:
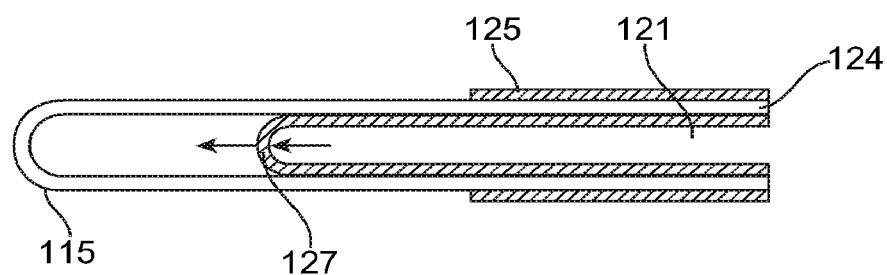
FIG. 43—depicts an applicator device with the actuators of both applicator tips engaged by an engagement element.

The device may optionally comprise an engagement element 127 for engaging and retracting the actuators on both applicators. FIG. 43 shows a device comprising a handle 115, two actuator-equipped applicator tips 124 and an engagement element 127 in contact with each applicator tip actuator 124. The engagement element is configured for movement along the longitudinal axis of the handle, wherein such movement may engage or retract the actuator resulting in compression or expansion of the spring-loaded applicator tip, respectively.

It may be desirable for the spring-assisted expansion of the applicator tip to be directionally biased to maximize contact with the wall of the nasal cavity and optimize contact pressure with the nasal turbinates. For example, the spring element can be dimensioned and configured such that the applicator expands laterally towards the turbinates of the nasal cavity. Alternatively or additionally, portions of the applicator tip may comprise an impermeable lining such that delivery of BoNT to certain portions of the nasal cavity is optimized and undesirable migration of BoNT solution is minimized.

Although toxins can be administered to the body to achieve a therapeutic benefit, the same toxins can cause local and systematic damage to non-targeted body tissues. Accordingly, it would also be desirable for the apparatus to be configured such that only the amount of toxin necessary to treat the nasal cavity is loaded on the applicator tip and applied to the nasal wall. It this embodiment, it would be desirable for the applicator to carry a predetermined quantity of toxin, wherein the predetermined quantity is the amount necessary to provide a therapeutic effect. It would also be desirable for the applicator to be configured such that most, if not all, of the toxin carried on the applicator is delivered to the nasal wall, wherein little to no toxin runs, escapes or migrates to non-target portions of body tissue.

Additionally, it would be desirable for the applicator to be configured to provide a controlled delivery of toxin to facilitate absorption of the toxin into the walls of the nasal cavity. An applicator providing a controlled delivery of toxin can be configured such that the rate of toxin delivery is proportionate with the rate of BoNT absorption across the nasal membrane. Such a controlled delivery will ensure that the toxin is absorbed into the nasal tissue and not dispersed elsewhere in the body.

An apparatus for treating a nasal cavity of a patient via a controlled and uniform delivery of BoNT may comprise an applicator having an inner member, an outer member and an impermeable lining, wherein the impermeable lining separates the inner member and outer member. In this embodiment, the outer member serves as a carrier for a toxin (e.g., BoNT). The outer member may comprise any material or structure for carrying BoNT such as an open cell foam (e.g., sponge), mesh pad, porous or perforated balloon, polymeric sheet having microchannels, bioresorbable coating or mucoadhesive surface having wells or open-faced chambers. The outer member may also comprise an array of microneedles to facilitate the passage of BoNT across the nasal membrane. The inner member is configured for occupying space when the applicator is positioned within the nasal cavity such that the outer member is placed in contact with the wall of the nasal cavity. The inner member may be any compliant material such as a sponge, balloon or foam rubber. The impermeable lining (e.g., tetrafluoroethylene) prevents the BoNT from retreating from the outer member to inner member and, accordingly, facilitates the transfer of BoNT from the applicator to the tissue of the nasal wall. As with applicator embodiments that have been previously discussed herein, the outer member can be pre soaked or filled with BoNT solution, infused with BoNT following placement in the nasal passageway, or pre-loaded with freeze-dried BoNT that can be reconstituted with infused saline.

In one embodiment, both the inner and outer members may comprise balloons, wherein the BoNT is carried in the space between the inner and outer balloons. The outer balloon can be a perforated polymer (e.g., polyethylene terephthalate or expanded polytetrafluoroethylene) for releasing BoNT in a controlled and uniform matter. The inner member can be a compliant balloon, wherein the volume occupied by the inner balloon can be adjusted by injecting a fluid (e.g., air or saline) into the inner balloon. In this configuration, the impermeable lining is comprised of the wall of the inner balloon and the applicator's BoNT carrying capacity is based on the volume of the outer balloon relative to that of the inner balloon. For example, an applicator could be configured to carry less BoNT by increasing the inner balloon's volume relative to the outer balloon's volume.

In a preferred embodiment, the inner member comprises (1) a low volume configuration to facilitate the applicator's insertion into and placement within the nasal passageway and (2) an expanded volume configuration for pressing the outer member against the walls of the nasal cavity. The expansion of the inner member relative to the outer member can also facilitate the controlled release of BoNT from the outer member. Once the applicator is in its expanded volume configuration, additional fluid can be infused into the inner member to reduce the volume of the outer member relative to the inner member, thereby forcing the BoNT from the outer member. In fact, the expansion of the inner member may be configured such that the resulting stretching and compression of the outer member causes a controlled release of BoNT from the outer member, wherein the rate of BoNT release is proportional to the inner member's rate of expansion. In the embodiment comprising an inner balloon and outer balloon, the expansion of the inner member can be facilitated by the introduction of fluid into the inner member. In other embodiments, the expansion of the inner member can be facilitated by a spring member.

In any of the embodiments discussed herein, it may be desirable to adapt the applicator to the geometry of the nasal cavity. For example, in embodiments comprising an outer member and inner member, the outer member can be configured to match the shape of the nasal cavity or portions of the nasal passageway following the expansion of the inner member. By achieving better contact, the delivery of toxin to and across the nasal membrane can be optimized.

To achieve a more focal treatment, the applicator tip can be equipped with a muco-adhesive pad that is pre-loaded with BoNT solution rather than a sponge. This pad can be configured to optimize the delivery of BoNT to the mucosa. Alternatively, the applicator tip may further comprise a bioabsorbable coating or film carrying BoNT. In this embodiment, the applicator tip may comprise a BoNT-loaded bioresorbable polymer that can be absorbed into the nasal cavity tissue. The tip can be configured such that the BoNT can be delivered to the nasal wall both immediately and as the coating is absorbed into the tissue.

Similar to the other devices discussed in this application, the device described with respect to FIGS. 33 and 34 can be used to deliver BoNT-LC to the nasal cavity instead of the BoNT intact molecule. In cases where this device is used to deliver BoNT-LC to the nasal cavity, any of the previously-described, energy-based delivery systems can be used to cause poration in the nasal tissue to facilitate delivery of the BoNT-LC to the tissue. Additionally or alternatively, this device can be equipped with an energy delivery element for causing poration in the target tissue in conjunction with delivery of BoNT-LC to the target tissue. For example, the device may comprise an electrode, antenna or ultrasonic transducer that is electrically connected to an energy generator configured for delivering energy via the energy delivery element to the target tissue at a voltage, amplitude, frequency, etc. sufficient to cause poration or permeablization in the target tissue.

Throughout this disclosure, the LC solution has typically been referred to as an infused, aerosolized or sprayed liquid. LC incorporated into coatings on devices has also been described. It should be noted, however, that other forms of LC delivery may be desirable.

For instance, commercially available botulinum toxins (such as Botox™—Allergan) are supplied as a dry lyophilized powder, and must be reconstituted prior to delivery by the addition of saline to the packaging vial. Similarly, light chain would be most readily available and stable in a powdered form. It may be desirable to spray or blow the powdered form of the LC into the target airways directly, without any reconstitution by liquid.

The lyophilized powder could also be formed into sheets, ribbons, pellets microspheres, or any other desirable form, and introduced to the target tissues.

Instead of a saline or low viscosity carrier, it may be desirable to deliver the light chain in a gel carrier, such as the types of gels which are commonly used for ultrasound coupling. Other appropriate gel carriers include such biocompatible gels as hyaluronic acid (HA). HA has the added benefit of being a thixotropic liquid—its viscosity drops as it begins to flow or as increasing shear stress is applied, and then returns to a higher viscosity state as it comes to rest. This would aid in delivery of the solution through catheters and the like, while allowing the gel to remain in place once delivered. HA is also extremely biocompatible, and would allow efficient ultrasonic coupling to the target tissues. The application of ultrasonic energy might also reduce the viscosity of the HA gel, possibly improving the delivery of toxin into the tissues.

It may also be desirable to incorporate the light chain into a foam, or to foam the LC solution upon or during delivery of the LC to the target tissues. Foams may better fill the entire targeted airway, and may trap water or coupling agents to allow efficient ultrasonic coupling. In a further embodiment, the foam may be energized within or as it exits the catheter shaft to further enhance the delivery of the LC to cells that are contacted by the energized foam and LC foam solution.

In addition to BTX-LC, it may be desirable to deliver additional agents to the nasal passages and sinuses prior to, coincident with, or after deliver of the LC. Adjunctive therapies may include agents designed to slow down or halt the motion of the cilia, in order to aid in delivery of the LC to the target tissues by prevention of their mobilization by the cilia. Agents known to slow or halt the motion of cilia include but are not limited to epinephrine dilutions of 1:1000 (which causes ciliary death), 1:10,000 (which causes reversible paralysis), 10% cocaine (induces paralysis) or 2.5% cocaine (slows or stops cilia).

Other adjunctive therapies may include the use of or pretreatment with mucolytics, which will thin mucus secretions within the nose and may allow better penetration of LC into the target cells.

Decongestants such as epinephrine also cause constriction of the vasculature in the nasal passages, which in addition to temporarily reducing swelling of the target tissues, may decrease the risks of LC entering the blood stream during poration and delivery. Epinephrine also constricts the blood vessels locally, which may increase the residence time of other locally delivered agents or decrease their likelihood of entering systemic circulation.

Steroids may be used to reduce swelling and inflammation prior to LC treatment in order to improve LC delivery to target tissues. In the abovementioned embodiments, it may be important to note that by far the most significant effects will be seen in areas where both the LC and the permeablizing energy are delivered. Therefore, although it may be best to deliver both LC and energy to substantially the same area, for reasons of anatomy, ease of delivery, etc., either the LC or the energy might be delivered more broadly, or to a somewhat different area. As an extreme example, the LC might be delivered systemically or to the entire respiratory pathway, followed by very localized delivery of energy to the desired area. Alternatively, the LC could be delivered to a specific sinus, followed by energy to the entire nose and sinus using a standardized external energy delivery mask.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of treating a nasal condition comprising:
   positioning one or more occlusion devices in a nasal cavity to fluidly isolate a treatment region therein from a remaining portion of the nasal cavity, the treatment region containing target cells; and
   introducing a toxin to the treatment region by a catheter while the one or more occlusion devices block the toxin from entering the remaining portion of the nasal cavity, wherein the toxin inhibits mucous secretion in the target.

2. The method of claim 1, wherein the toxin comprises a light chain fragment of a neurotoxin substantially free of heavy chain fragments of the neurotoxin.

3. The method of claim 2, wherein the neurotoxin consists of botulinum toxin.

4. The method of claim 3, wherein the light chain fragment is derived from at least one of botulinum toxins A, B, C, D, E, F, and G.

5. The method of claim 1, wherein the one or more occlusion devices comprise one or more balloons.

6. The method of claim 5, further comprising inflating the one or more balloons to isolate the treatment region.

7. The method of claim 1, wherein the one or more occlusion devices comprise one or more plugs positioned to block a nasal passage of the patient.

8. The method of claim 1, wherein the toxin is introduced by a balloon on the catheter.

9. The method of claim 8, wherein, the balloon comprises one or more pores and the toxin is introduced through the pores of the balloon.

10. The method of claim 1, wherein the toxin is introduced through a needle on the catheter.

11. The method of claim 1, wherein the toxin is aerosolized from the catheter.

12. The method of claim 1, further comprising applying energy to the target cells under conditions which cause potation of the cell membranes to enhance delivery of the toxin.

13. The method of claim 12, wherein applying energy to the target cells comprises applying an electric pulse of between 1 V and 500 V to the target cells.

14. The method of claim 13, wherein the electric pulse comprises an RF signal.

15. The method of claim 13, wherein the electric pulse is applied for durations between 5 microseconds to 100 milliseconds.

16. The method of claim 13, wherein the electric pulse is produced by a DC power source.

17. The method of claim 13, wherein the electric pulse is produced by an AC power source.

18. The method of claim 12, wherein applying energy to the target cells comprises applying acoustic energy to the target cells.

19. The method of claim 18, wherein the acoustic energy comprises ultrasonic energy.

20. The method of claim 12, wherein applying energy to the target cells comprises applying electromagnetic energy to the target cells.

21. The method of claim 20, wherein the electromagnetic energy comprises microwaves.

22. The method of claim 20, wherein the electromagnetic energy comprises X-rays.

23. The method of claim 12, wherein energy is selectively applied to the target cells.

24. The method of claim 12, wherein energy is non-selectively applied to the target cells.

25. The method of claim 1, wherein the treatment region comprises at least one paranasal sinus, a main nasal passage, or a nasal turbinate.

26. The method of claim 1, wherein the treatment region comprises substantially the entire nasal cavity.

27. The method of claim 1, wherein the treatment region comprises substantially the nasopharynx.

28. The method of claim 1, wherein the target cells comprise epithelial or goblet cells.

29. The method of claim 1, wherein the patient suffers from or is at risk of suffering from rhinorrhea.

30. The method of claim 1, wherein the patient suffers from or is at risk of suffering from sinus headaches or migraine headaches.

31. A method of treating a nasal condition in a patient, said method comprising:
   introducing a foam carrier comprising a toxin to a treatment region in a nasal cavity containing target cells, wherein the toxin is delivered from the foam carrier to the target cells so as to inhibit mucous secretion in the target cells.

32. The method of claim 31, wherein the toxin comprises a light chain fragment of a neurotoxin substantially free of heavy chain fragments of the neurotoxin.

33. The method of claim 32, wherein the neurotoxin consists of botulinum toxin.

34. The method of claim 33, wherein the light chain fragment is derived from at least one of botulinum toxins A, B, C, D, E, F, and G.

35. The method of claim 31, further comprising filling a targeted airway of the nasal cavity of the patient with the foam carrier.

36. The method of claim 35, further comprising fluidly isolating a treatment region of the nasal cavity, wherein the toxin is introduced into the treatment region.

37. The method of claim 31, wherein the foam carrier remains in place in the nasal cavity following introduction while the toxin is delivered to the target cells.

38. The method of claim 31, further comprising applying energy to the foam carrier to enhance delivery of the toxin to the cells.

39. The method of claim 38, wherein ultrasonic energy is applied to the foam carrier to enhance delivery of the toxin to the cells.

40. The method of claim 31, wherein the foam carrier is introduced by a catheter.

41. The method of claim 40, wherein the foam carrier is introduced by a balloon on the catheter.

42. The method of claim 41, wherein the balloon comprises one or more pores and the foam carrier is introduced through the pores of the balloon.

43. The method of claim 40, wherein the foam carrier is introduced through a needle on the catheter.

44. The method of claim 31, further comprising applying energy to the target cells to enhance delivery of the toxin to the cells.

45. The method of claim 44, wherein the energy is applied to the target cells under conditions which cause poration of the cell membranes to enhance delivery of the toxin.

46. The method of claim 44, wherein applying energy to the target cells comprises applying an electric pulse of between 1 V and 500 V to the target cells.

47. The method of claim 46, wherein the electric pulse comprises an RF signal.

48. The method of claim 46, wherein the electric pulse is applied for durations between 5 microseconds to 100 milliseconds.

49. The method of claim 46, wherein the electric pulse is produced by a DC power source.

50. The method of claim 46, wherein the electric pulse is produced by an AC power source.

51. The method of claim 44, wherein applying energy to the target cells comprises applying acoustic energy to the target cells.

52. The method of claim 51, wherein the acoustic energy comprises ultrasonic energy.

53. The method of claim 44, wherein applying energy to the target cells comprises applying electromagnetic energy to the target cells.

54. The method of claim 53, wherein the electromagnetic energy comprises microwaves.

55. The method of claim 53, wherein the electromagnetic energy comprises X-rays.

56. The method of claim 44, wherein energy is selectively applied to the target cells.

57. The method of claim 44, wherein energy is non-selectively applied to the target cells.

58. The method of claim 31, wherein the treatment region comprises at least one paranasal sinus, a main nasal passage, or a nasal turbinate.

59. The method of claim 31, wherein the treatment region comprises substantially the entire nasal cavity.

60. The method of claim 31, wherein the treatment region comprises substantially the nasopharynx.

61. The method of claim 31, wherein the target cells comprise epithelial or goblet cells.

62. The method of claim 31, wherein the patient suffers from or is at risk of suffering from rhinorrhea.

63. The method of claim 31, wherein the patient suffers from or is at risk of suffering from sinus headaches or migraine headaches.

64. The method of claim 36, wherein fluidly isolating a treatment region of the nasal cavity comprises positioning one or more occlusion devices in the nasal cavity.

65. A method of treating a nasal condition comprising:
positioning one or more occlusion devices in a nasal cavity to fluidly isolate a treatment region therein from a remaining portion of the nasal cavity, the treatment region containing target cells and comprising at least one paranasal sinus; and
introducing a toxin to the treatment region while the one or more occlusion devices block the toxin from entering the remaining portion of the nasal cavity, wherein the xin inhibits mucous secretion in the target.

66. The method of claim 65, wherein the toxin comprises a light chain fragment of a neurotoxin substantially free of heavy chain fragments of the neurotoxin.

67. The method of claim 66, wherein the neurotoxin consists of botulinum toxin.

68. The method of claim 65, wherein the one or more occlusion devices comprise one or more balloons.

69. The method of claim 65, wherein the toxin is introduced by a catheter.

70. The method of claim 65, further comprising applying energy to the target cells under conditions which cause poration of the cell membranes to enhance deliver of the toxin.

71. The method of claim 65, wherein the target cells comprise epithelial or goblet cells.

72. The method of claim 65, wherein the patient suffers from or is at risk of suffering from rhinorrhea, sinus headache or migraine headaches.

* * * * *